(12) United States Patent
Brown et al.

(10) Patent No.: US 8,629,255 B2
(45) Date of Patent: Jan. 14, 2014

(54) NUCLEIC ACID MOLECULES CONFERRING ENHANCED ETHANOL TOLERANCE AND MICROORGANISMS HAVING ENHANCED TOLERANCE TO ETHANOL

(75) Inventors: Steven Brown, Knoxville, TN (US); Adam Guss, Knoxville, TN (US); Shihui Yang, Knoxville, TN (US); Tatiana Karpinets, Louisville, TN (US); Lee Lynd, Meriden, NH (US); Xiongjun Shao, White River Junction, VT (US)

(73) Assignee: UT-Battelle, LLC, Oak Ridge, TN (US)

( * ) Notice: Subject to any disclaimer, the term of this patent is extended or adjusted under 35 U.S.C. 154(b) by 28 days.

(21) Appl. No.: 13/112,641

(22) Filed: May 20, 2011

(65) Prior Publication Data

US 2011/0287499 A1    Nov. 24, 2011

Related U.S. Application Data

(60) Provisional application No. 61/346,660, filed on May 20, 2010.

(51) Int. Cl.
*C07H 21/00* (2006.01)
*C12P 7/02* (2006.01)
*C12N 1/00* (2006.01)
*C12N 15/75* (2006.01)
*C12N 1/15* (2006.01)

(52) U.S. Cl.
USPC .. 536/23.2; 435/155; 435/252.3; 435/254.11; 435/320.1

(58) Field of Classification Search
None
See application file for complete search history.

(56) References Cited

PUBLICATIONS

Parsch et al Gen.Soc. Am. 2000,156, pp. 219-227.*

* cited by examiner

*Primary Examiner* — Tekchand Saidha
*Assistant Examiner* — Md. Younus Meah
(74) *Attorney, Agent, or Firm* — Scully, Scott, Murphy & Presser, P.C.

(57) ABSTRACT

The present invention provides isolated nucleic acid molecules which encode a mutant acetaldehyde-CoA/alcohol dehydrogenase or mutant alcohol dehydrogenase and confer enhanced tolerance to ethanol. The invention also provides related expression vectors, genetically engineered microorganisms having enhanced tolerance to ethanol, as well as methods of making and using such genetically modified microorganisms for production of biofuels based on fermentation of biomass materials.

27 Claims, 16 Drawing Sheets

Original protein sequence (SEQ ID NO: 1): >Cthe_0423_ iron-containing alcohol dehydrogenase;
aldeh  - 531351: 533972  MW: 96010.88

MTKIANKYEVIDNVEKLEKALKRLREAQSVYATYTQEQVDKIFFEAAMAANKMRIPLAKM
AVEETGMGVVEDKVIKNHYASEYIYNAYKNTKTCGVIEEDPAFGIKKIAEPLGVIAAVIP
TTNPTSTAIFKTLIALKTRNAIIISPHPRAKNSTIEAAKIVLEAAVKAGAPEGIIGWIDV
PSLELTNLVMREADVILATGGPGLVKAAYSSGKPAIGVGAGNTPAIIDDSADIVLAVNSI
IHSKTFDNGMICASEQSVIVLDGVYKEVKKEFEKRGCYFLNEDETEKVRKTIIINGALNA
KIVGQKAHTIANLAGFEVPETTKILIGEVTSVDISEEFAHEKLCPVLAMYRAKDFDDALD
KAERLVADGGFGHTSSLYIDTVTQKEKLQKFSERMKTCRILVNTPSSQGGIGDLYNFKLA
PSLTLGCGSWGGNSVSDNVGVKHLLNIKTVAERRENMLWFRTPEKIYIKRGCLPVALDEL
KNVMGKKKAFIVTDNFLYNNGYTKPITDKLDEMGIVHKTFFDVSPDPSLASAKAGAAEML
AFQPDTIIAVGGGSAMDAAKIMWVMYEHPEVDFMDMAMRFMDIRKRVYTFPKMGQKAYFI
AIPTSAGTGSEVTPFAVITDEKTGIKYPLADYELLPDMAIVDADMMMNAPKGLTAASGI d
ALThALEAYVSMLATDYTDSLALRAIKMIFEYLPRAYENGASDPVAREKMANAATIAGMA
FANAFLGVChSMA*H*KLGAFYHLPhGVANALMINEVIRFNSSEAPTKMGTFPQYDHPRTLE
RYAEIADYIGLKGKNNEEKVENLIKAIDELKEKVGIRKTIKDYDIDEKEFLDRLDEMVEQ
AFDDQCTGTNPRYPLMNEIRQMYLNAYYGGAKK

The Protein sequence after SNP changes (SEQ ID NO: 2): >Cthe_0423_2_SNPs

MTKIANKYEVIDNVEKLEKALKRLREAQSVYATYTQEQVDKIFFEAAMAANKMRIPLAKM
AVEETGMGVVEDKVIKNHYASEYIYNAYKNTKTCGVIEEDPAFGIKKIAEPLGVIAAVIP
TTNPTSTAIFKTLIALKTRNAIIISPHPRAKNSTIEAAKIVLEAAVKAGAPEGIIGWIDV
PSLELTNLVMREADVILATGGPGLVKAAYSSGKPAIGVGAGNTPAIIDDSADIVLAVNSI
IHSKTFDNGMICASEQSVIVLDGVYKEVKKEFEKRGCYFLNEDETEKVRKTIIINGALNA
KIVGQKAHTIANLAGFEVPETTKILIGEVTSVDISEEFAHEKLCPVLAMYRAKDFDDALD
KAERLVADGGFGHTSSLYIDTVTQKEKLQKFSERMKTCRILVNTPSSQGGIGDLYNFKLA
PSLTLGCGSWGGNSVSDNVGVKHLLNIKTVAERRENMLWFRTPEKIYIKRGCLPVALDEL
KNVMGKKKAFIVTDNFLYNNGYTKPITDKLDEMGIVHKTFFDVSPDPSLASAKAGAAEML
AFQPDTIIAVGGGSAMDAAKIMWVMYEHPEVDFMDMAMRFMDIRKRVYTFPKMGQKAYFI
AIPTSAGTGSEVTPFAVITDEKTGIKYPLADYELLPDMAIVDADMMNAPKGLTAASGID
ALTHALEAYVSMLATDYTDSLALRAIKMIFEYLPRAYENGASDLVAREKMANAATIAGMA
FANAFLGVCHSMARKLGAFYHLPHGVANALMINEVIRFNSSEAPTKMGTFPQYDHPRTLE
RYAEIADYIGLKGKNNEEKVENLIKAIDELKEKVGIRKTIKDYDIDEKEFLDRLDEMVEQ
AFDDQCTGTNPRYPLMNEIRQMYLNAYYGGAKK

Figure 2A

Wild-type Cthe_0423 nucleotide sequence (SEQ ID NO: 3):

```
ATGACGAAAATAGCGAATAAATACGAAGTTATTGATAATGTTGAAAAGCTTGAAAAGGCTTTGAAACGTTTAAG
AGAAGCTCAAAGTCTTTATGCAACCTATACACAGGAGCACCTTGACAAAATTTTCTTTGAGCCCGCAATGGCGG
CCAATAAAATGAGAATTCCTCTTGCCAAAATGGCTGTGGAGGAAACAGGCATGGGAGTGGTTGAAGACAAGGTT
ATCAAAAACCACTATGCTTCTGAGTATATCTATAATGCGTACAAAAACACTAAAACCTGCGGTGTTATTGAAGA
GGACCCTGCTTTCGGTATTAAAAAAATAGCAGAGCCTTTGGGGGTTATTGCGGCGGTTATACCTACTACGAATC
CGACATCGACAGCAATCTTTAAGACTCTTATTGCATTAAAGACGAGAAATGCAATTATTATAAGCCCACACCCC
AGGGCAAAAAACTCAACGATAGAAGCGGCGAAAATTGTTTTGGAGGCGGCCGTTAAAGCCGGTGCTCCGGAAGG
CATCATTGGCTGGATTGATGTGCCGAGCCTTGAACTTACCAACCTGGTAATGAGAGAAGCAGATGTGATTCTCG
CAACAGGCGGTCCCGGACTGGTTAAAGCAGCTTACTCTTCGGGCAAACCGGCTATTGGTGTCGGAGCGGGCAAT
ACTCCTGCAATTATTCATGATTCGGCCGACATTGTCTTGGCAGTGAACTCAATAATACATTCAAAAACTTTCGA
CAACGGTATGATTTGTGCTTCAGAGCAATCGGTCATTGTTCTGGACGGGGTATATAAAGAGGTAAAAAAAGAAT
TTGAAAAAGAGGATGCTATTTCTTAAATGAAGATGAAACTGAAAAGGTAAGAAAAACAATTATAATAAACGGT
GCGTTAAATGCCAAGATAGTAGGTCAGAAAGCTCACACAATTGCAAACCTTGCAGGTTTTGAGGTACCCGAGAC
TACAAAAATTCTGATAGCCGAAGTTACCAGCGTGGATATTTCCGAAGAATTTGCCCACCAAAAGTTGTGCCCGG
TACTGGCAATGTACAGGGCAAAGGATTTTGACGATGCCCTTGATAAAGCAGAAAGGTTGGTAGCTGACGGTGGA
TTTGGCCATACTTCGTCACTTTATATAGATACGGTAACACAGAAAGAGAAACTTCAGAAATTCTCTGAAAGGAT
GAAAACCTGCCGTATATTGGTTAATACGCCGTCATCCCAGGGAGGTATCGGTGACCTTTACAACTTCAAGCTTG
CTCCGTCTCTCACCCTCGGCTGCGGTTCCTGGGGAGGAAATTCAGTTTCCGACAATGTGGGAGTCAAGCATTTG
TTAAACATTAAAACAGTTGCCGAGAGGAGAGAGAACATGCTCTGGTTCAGAACACCTGAAAAGATTTATATAAA
AAGAGGTTGTCTGCCTGTTGCATTGGATGAGCTTAAAAATGTAATGGGTAAAAAGAAAGCATTTATTGTAACGG
ATAACTTCTGTACAATAACGGCTACACCAAGCCGATTACGGATAAGCTGGATGAAATGGGAATTGTGCACAAG
ACCTTCTTTGATGTCTCTCCAGACCCATCCCTTGCATCTCCCAAAGCCGGTGCGGCACAAATCCTGGCTTTCCA
GCCTGACACCATAATTGCGGTCGGCGGCGGATCTGCCATGGACGCGGCCAAAATCATGTGGGTGATGTATGAAC
ATCCGGAAGTTGACTTTATGGACATGGCAATGAGATTTATGGATATAAGAAAGAGAGTTACACCTTCCCGAAG
ATGGGACAGAAGGCATACTTTATCGCAATTCCGACTTCCGCGGGTACAGGTTCAGAAGTGACACCTTTTGCGGT
TATTACTGATGAAAAACAGGAATTAAATACCCTCTGGCCGACTATGAATTGTTGCCGGACATGGCTATTGTAG
ATGCCGATATGATGATGAATGCTCCAAAGGGACTTACCGCAGCTTCCGGTATAGACGCATTGACCCACGCTCTG
GAAGCCTATGTTTCAATGCTTGCGACCGACTATACGGATAGCCTTGCCCTTCGTGCAATAAAGATGATATTTGA
ATATCTCCCGAGAGCCTATGAAAACGGTGCAAGTGACCCGGTTGCAAGAGAGAAAATGGCCAATGCCGCAACAA
TAGCCCGGAATGGCTTTTCCCAATGCCTTTTTGGGTGTATCCCATTCAATGGCGCACAAACTGCCTGCTTTTTAT
CACCTGCCCCACGGTGTTGCCAATGCACTTATGATAAACGAAGTAATCAGATTCAACTCATCCGAGGCTCCGAC
CAAGATGGGTACTTTCCCGCAGTATGACCATCGCGCACGCTGGAAAGGTATGCAGAAATGCCGATTATATCG
GACTTAAGGGCAAGAATAACGAAGAAAAGTTGAAAACTTGATTAAAGCTATTGATGAGCTTAAAGAAAAGGTG
GGCATCAGGAAGACCATCAAAGATTATGACATAGATGAAAACGAATTTTTGGACACACTCCACCAAATGGTGGA
ACAGGCTTTTGACGACCAGTGCACAGGTACAAATCCAAGATACCCGCTTATGAATGAAATCAGGCAAATGTATC
TGAACGCTTATTACGGAGGTGCGAAGAAATGA
```

Figure 2B

Mutant Cthe_0423 nucleotide sequence (SEQ ID NO: 4):

```
ATGACGAAAATAGCGAATAAATACGAAGTTATTGATAATGTTGAAAAGCTTGAAAAGGCTTTGAAACGTTTAAGAGA
AGCTCAAAGTGTTTATGCAACCTATACACAGGAGCAGGTTGACAAAATTTTCTTTGAGGCGGCAATGGCGGCCAATA
AAATGAGAATTCCTCTTCCCAAAATGCCTGTGGAGCAAACAGCCATGGGAGTGGTTCAAGACAAGCTTATCAAAAAC
CACTATGCTTCTGAGTATATCTATAATGCGTACAAAAACACTAAAACCTGCGGTGTTATTGAAGAGGACCCTGCTTT
CGGTATTAAAAAAATAGCAGAGCCTTTGGGGGTTATTGCGGCGGTTATACCTACTACGAATCCGACATCGACAGCAA
TCTTTAAGACTCTTATTGCATTAAAGACGAGAAATGCAATTATTATAAGCCCACACCCCAGGGCAAAAAACTCAACG
ATACAAGCCGCCAAAATTGTTTTGCACGCGGCCGTTAAAGCCCGTTGCTCCGGAACGCATCATTGCTGGATTCATGT
GCCGAGCCTTGAACTTACCAACCTGGTAATGAGAGAAGCAGATGTGATTCTCGCAACAGGCGGTCCCGGACTGGTTA
AAGCAGCTTACTCTTCGGGCAAACCGGCTATTGGTGTCGGAGCGGGCAATACTCCTGCAATTATTGATGATTCGGCC
GACATTGTCTTGGCAGTGAACTCAATAATACATTCAAAAACTTTCGACAACGGTATGATTGTGCTTCAGAGCAATC
GGTCATTGTTCTGGACGGGGTATATAAAGAGGTAAAAAAAGAATTTGAAAAAAGAGGATGCTATTTCTTAAATGAAG
ATGAAACTGAAAAGGTAAGAAAAACAATTATAATAAACGGTGCGTTAAATGCCAAGATAGTAGGTCAGAAAGCTCAC
ACAATTGCAAACCTTGCAGGTTTTGAGGTACCCGAGACTACAAAAATTCTGATAGGCGAAGTTACCAGCGTGGATAT
TTCCGAAGAATTTGCCCACCAAAAGTTGTGCCCCGTACTGCCAATGTACAGGGCAAAGGATTTTGACGATCCCCTTG
ATAAAGCAGAAAGGTTGGTAGCTGACGGTGGATTTGGCCATACTTCGTCACTTTATATAGATACGGTAACACAGAAA
GAGAAACTTCAGAAATTCTCTGAAAGGATGAAAACCTGCCGTATATTGGTTAATACGCCGTCATCCCAGGGAGGTAT
CGGTGACCTTTACAACTTCAAGCTTGCTCCGTCTCTCACCCTCGGCTGCGGTTCCTGGGGAGGAAATTCAGTTTCCG
ACAATGTGGGAGTCAAGCATTTGTTAAACATTAAAACAGTTGCCGAGAGGAGAGAGAACATGCTCTGGTTCAGAACA
CCTGAAAAGATTTATATAAAAAGAGGTTGTCTGCCTGTTGCATTGGATGAGCTTAAAAATGTAATGGGTAAAAAGAA
AGCATTTATTGTAACGGATAACTTCCTGTACAATAACGGCTACACCAAGCCGATTACGGATAAGCTGGATGAAATGG
GAATTGTGCACAAGACCTTCTTTGATGTGTCTCCAGACCCATCCCTTGCATCTGCCAAAGCCGGTGCGGCAGAAATG
CTGGCTTTCCAGCCTGACACCATATGCGGTCGGCGCCGGCATCTGCCATGGACGCCGGCCAAAATCATGTGGCTCAT
GTATGAACATCCGGAAGTTGACTTTATGGACATGGCAATGAGATTTATGGATATAAGAAAGAGAGTTTACACCTTCC
CGAAGATGGGACAGAAGGCATACTTTATCGCAATTCCGACTTCCGCGGGTACAGGTTCAGAAGTGACACCTTTTGCG
GTTATTACTGATGAAAAAACAGGAATTAAATACCCTCTGGCCGACTATGAATTGTTGCCGGACATGGCTATTGTAGA
TCCCGATATGATGATGAATGCTCCAAAGCGACTTACCCCAGCTTCCGGTATAGACGCATTGACCCACGCTCTCGAAG
CCTATGTTTCAATGCTTGCGACCGACTATACGGATAGCCTTGCCCTTCGTGCAATAAAGATGATATTTGAATATCTC
CCGAGAGCCTATGAAAACGGTGCAAGTGACCTGGTTGCAAGAGAGAAAATGGCCAATGCCGCAACAATAGCCGGAAT
GGCTTTTGCCAATGCCTTTTGGGTGTATGCCATTCAATGGCGCGCAAACTGGGTGCTTTTATCACCTGCCCCACG
GTGTTGCCAATGCACTTATGATAAACGAAGTAATCAGATTCAACTCATCCGAGGCTCCGACCAAGATGGGTACTTTC
CCGCAGTATGACCATCCGCGCACGCTGGAAAGGTATGCAGAAATTGCCGATTATATCGGACTTAAGGGCAAGAATAA
CGAAGAAAAGTTGAAAACTTGATTAAAGCTATTGATGAGCTTAAAGAAAAGGTGGGCATCAGGAAGACCATCAAAG
ATTATGACATAGATGAAAACGAATTTTCGACAGACTGGACCAAATGGTCGAACAGGCTTTTGACCACCAGTCCACA
GGTACAAATCCAAGATACCCGCTTATGAATGAAATCAGGCAAATGTATCTGAACGCTTATTACGGAGGTGCGAAGAA
ATGA
```

Figure 2C

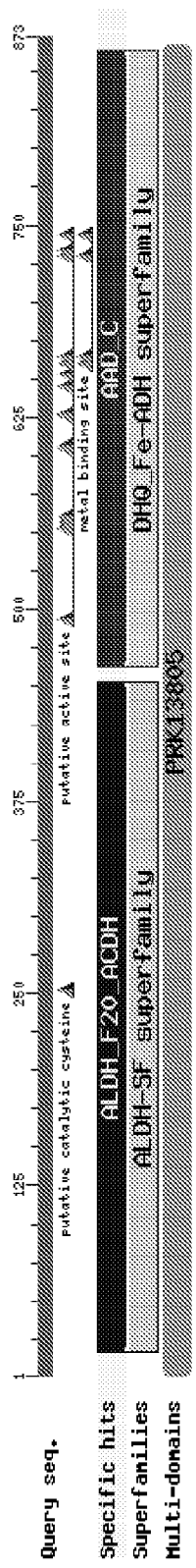
Figure 3
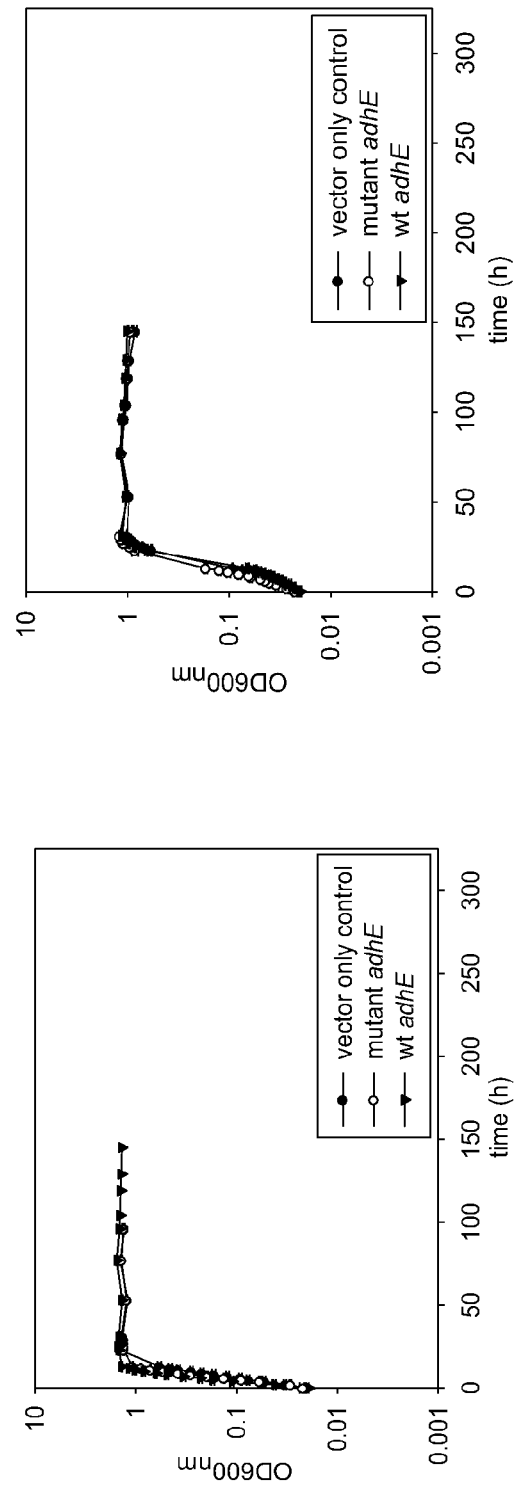
Figure 4A
Figure 4B

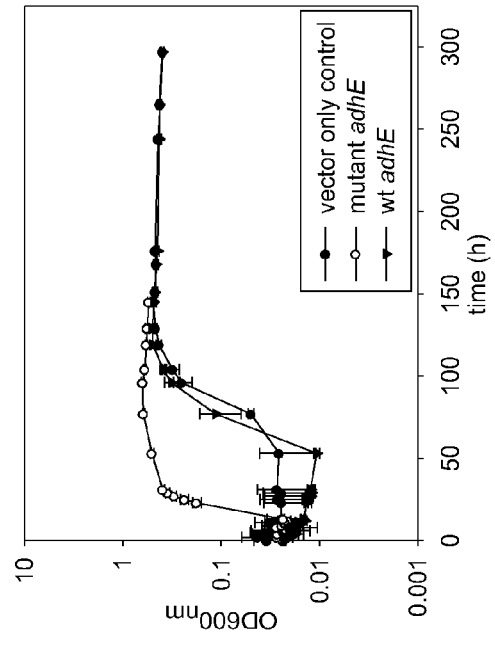
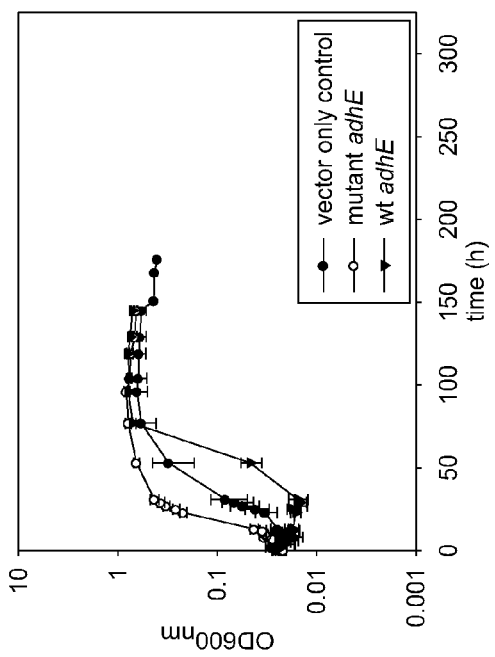
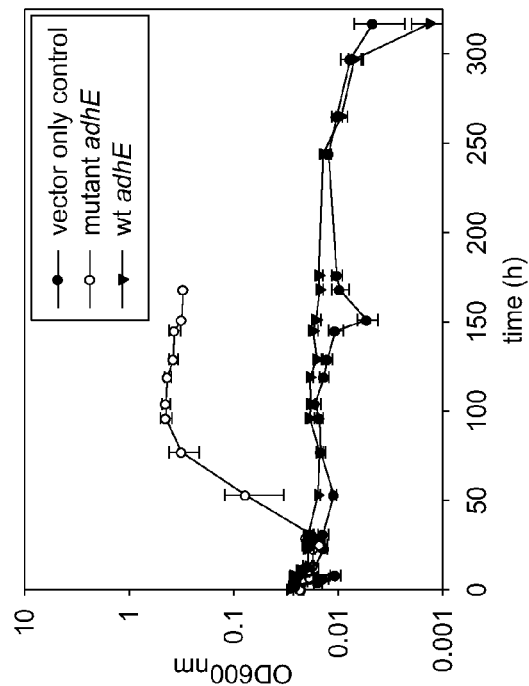
Figure 4C
Figure 4D
Figure 4E plasmid pAMG205 (SEQ ID NO:5)

```
aaacccgctgatcctagagggccgcatcatgtaattagttatgtcacgcttacattcacgcctccccccacatccgctctaaccg
aaaaggaaggagttagacaacctgaagtctaggtccctatttattttttatagttatgttagtattaagaacgttatttatattt
caaatttttcttttttttctgtacagacgcgtgtacgcatgtaacattatactgaaaaccttgcttgaagggttttgggacgctc
gaaggctttaatttgcaagctgcggccctgcattaatgaatcggccaacgcgcggggagaggcggtttgcgtattgggcgctcttc
cgcttcctcgctcactgactcgctgcgctcggtcgttcggctgcggcgagcggtatcagctcactcaaagcggtaatacggttat
ccacagaatcaggggataacgcaggaaagaacatgtgagcaaaaggccagcaaaagcccaggaaccgtaaaaaggccgcgttgctg
gcgtttttccataggctccgcccccctgacgagcatcacaaaaatcgacgctcaagtcagaggtggcgaaacccgacaggactata
aagataccaggcgtttccccctggaagctccctcgtgcgctctcctgttccgaccctgccgcttaccggatacctgtccgcctttc
tcccttcgggaagcgtggcgctttctcatagctcacgctgtaggtatctcagttcggtgtaggtcgttcgctccaagctgggctgt
gtgcacgaaccccccgttcagcccgaccgctgcgccttatccggtaactatcgtcttgagtccaacccggtaagacacgacttatc
gccactggcagcagccactggtaacaggattagcagagcgaggtatgtaggcggtgctacagagttcttgaagtggtggcctaact
acggctacactagaaggacagtatttggtatctgcgctctgctgaagccagttaccttcggaaaaagagttggtagctcttgatcc
ggcaaacaaaccaccgctggtagcggtggtttttttgtttgcaagcagcagattacgcgcagaaaaaaaggatctcaagaagatcc
tttgatcttttctacggggtctgacgctcagtggaacgaaaactcacgttaagggattttggtcatgagattatcaaaaaggatct
tcacctagatccttttaaattaaaaatgaagttttaaatcaatctaaagtatatatgagtaaacttggtctgacagttaccaatgc
ttaatcagtgaggcacctatctcagcgatctgtctatttcgttcatccatagttgcctgactccccgtcgtgtagataactacgat
acgggagcgcttaccatctggccccagtgctgcaatgataccgcgagacccacgctcaccggctccagatttatcagcaataaacc
agccagccggaagggccgagcgcagaagtggtcctgcaactttatccgcctccatccagtctattaattgttgccgggaagctaga
gtaagtagttcgccagttaatagtttgcgcaacgttgttggcattgctacaggcatcgtggtgtcactctcgtcgtttggtatggc
ttcattcagctccggttcccaacgatcaaggcgagttacatgatcccccatgttgtgcaaaaaagcggttagctccttcggtcctc
cgatcgttgtcagaagtaagttggccgcagtgttatcactcatggttatggcagcactgcataattctcttactgtcatgccatcc
gtaagatgcttttctgtgactggtgagtactcaaccaagtcattctgagaatagtgtatgcggcgaccgagttgctcttgcccggc
gtcaatacgggataatagtgtatcacatagcagaactttaaaagtgctcatcattggaaaacgttcttcggggcgaaaactctcaa
ggatcttaccgctgttgagatccagttcgatgtaacccactcgtgcacccaactgatcttcagcatcttttactttcaccagcgtt
tctgggtgagcaaaaacaggaaggcaaaatgccgcaaaaaagggaataagggcgacacggaaatgttgaatactcatactcttcct
ttttcaatggtaataactgatataattaaattgaagctctaatttgtgagtttagtatacatgcatttacttataatacagttttt
ttagttttgctggccgcatcttctcaaatatgcttcccagcctgcttttctgtaacgttcaccctctaccttagcatcccttccct
ttgcaaatagtcctcttccaacaataataatgtcagatcctgtagagaccacatcatccacggttctatactgttgacccaatgcg
tctcccttgtcatctaaacccacaccggtgtcataatcaaccaatcgtaaccttcatctcttccacccatgtctctttgagcaat
aaagccgataacaaaatcttttgtcgctcttcgcaatgtcaacagtaccttagtatattctccagtagataggaggcccttgcatg
acaattctgctaacatcaaaaggcctctaggttcctttgttacttcttctgcgcctgcttcaaaccgctaacaataacctggcgcc
accacaccgtgtgcattcgtaatgtctgccattctgctattctgtatacacccgcagagtactgcaatttgactgtattaccaat
gtcagcaaattttctgtcttcgaagagtaaaaaattgtacttggcggataatgcctttagcggcttaactgtgccctccatggaaa
aatcagtcaagatatccacatgtgttttagtaaacaaattttgggacctaatgcttcaactaactccagtaattccttggtggta
cgaacatccaatgaagcacacaagtttgtttgcttttcgtgcatgatattaaatagcttggcagcaacaggactaggatgagtagc
agcacgttccttatatgtagctttcgacatgatttatcttcgtttcctgcaggttttttgttctgtgcagttgggttaagaatactg
ggcaattcatgtttcttcaacactacatatgcgtatatataccaatctaagtctgtgctccttcctttgtttcttccttctgttcg
gagattaccgaatcaaaaaaatttcaaagaaaccgaaatcaaaaaaaaagaataaaaaaaaaatgatgaattgaattgaaaagctag
cttatcgatgggtccttttcatcacgtgctataaaaataattataatttaaattttttaatataaatatataaattaaaaatagaa
agtaaaaaagaaattaaagaaaaaatagtttttgttttccgaagatgtaaaagactctaggggatcgccaacaaatactaccttt
ttatcttgctcttcctgctctcaggtattaatgccgaattgtttcatcttgtctgtgtagaagaccacacacgaaaatcctgtgat
tttacattttacttatcgtaatcgaatgtatatctatttaatctgcttttcttgtctaataaatatatatgtaaagtacgcttt
tgttgaaatttttttaaacctttgttttattttttttttcttcattccgtaactcttctaccttcttttatttactttctaaaatccaaa
tacaaaacataaaaataaatcacagagtaaattcccaaattattccatcattaaaagatacgaggcgcgtgtaagttacaggc
aagcgatccgtccgccggcgaacgtggcgagaaaggaagggaagaaagcgaaaggagcggggctagggcggtgggaagtgtaggg
gtcacgctggcgtaaccaccacaccgccgcgcttaatggggcgctacagggcgcgtgggatgatccactagtgaatttaggag
gcttacttgtctgctttcttcattagaatcaatcctttttaaaagtcaatcccgtttgttgaactactcttaataaaataatttt
ttccgttcccaattccacattgcaataatagaaaatccatcttcatcggcttttttcgtcatcatctgtatgaatcaaatcgccttc
ttctgtgtcatcaaggtttaattttttatgtatttcttttaacaaaccaccataggagattaaccttttacggtgtaaaccttcct
ccaaatcagacaaacgtttcaaattcttttcttcatcatcggtcataaaatccgtatcctttacaggatattttgcagtttcgtca
attgccgattgtatatccgatttatatttattttcggtcgatcatttgaacttttacatttggatcatagtctaatttcattgc
cttttccaaaattgaatccattgttttttgattcacgtagttttctgtattcttaaaataagttggttccacacataccaatacat
gcatgtgctgattataagaattatctttattatttattgtcacttccgttgcacgcataaaaccaacaagatttttattaattttt
ttatattgcatcattcggcgaaatccttgagccatatctgacaaactcttatttaattcttcgccatcataaacattttaactgt
taatgtgagaaacaaccaacgaactgttggcttttgtttaataacttcagcaacaaccttttgtgactgaatgccatgtttcattg
ctctcctccagttgcacattggacaaagcctggatttacaaaaccacactcgatacaactttctttcgcctgtttcacgattttgt
ttatactctaatatttcagcacaatcttttactctttcagcttttttaaattcaagaatatgcagaagttcaaagtaatcaacatt
agcgatttctttttctctccatgtctcacttttccacttttttgtcttgtccactaaaacccttgattttcatctgaataaatgc
tactattaggacacataatattaaaagaaaccccatctatttagttatttgtttggtcacttataactttaacagatgggttttt
```

Figure 5A

```
tctgtgcaaccaattttaagggttttcaatactttaaaacacatacataccaacacttcaacgcacctttcagcaactaaataaa
aatgacgttatttctatatgtatcaagaatagaaagaactcgttttcgctacgctcaaaacgcaaaaaaagcactcattcgagtg
cttttcttatcgctccaaatcatgcgattttttcctctttgcttttctttgctcacgaagttctcgatcacgctgcaaaacatct
tgaagcgaaaaagtattcttcttttcttccgatcgctcatgctgacgcacgaaaagccctctaggcgcataggaacaactcctaaa
tgcatgtgagggggttttctcgtccatgtgaacagtcgcatacgcaatattttgtttcccatagctagtaagcttggatcctcgcga
ggccggccagtattctgacatgggtgtatcaataacccatgcgtttccgtattgtatcggaatggtttcggacagggcggtgggaa
tagacatggaaaagattttttgcccgaggatgcattgataaagtatttcttttccgaaagagaggaaaagattctaaagagtttt
ggaaatactgatgaatattgtgtgcagagtacaattctatggacaagaaagaggctttgtcaaaacttttcgtctgggaatgag
gatggattttaaaaagctggatacttggaggacgaggtggttttcaggaaacaaacagggcgcgtctgttttctttatatgca
ataattactgtatctctctggcattgccaggttttaataaagattaaaattattgactagaaataaaaaaattgtccataatatta
atggacaaaaaacaaagaattacatcaaaggaagataaaaatactttgttaaaaaattaattatttttatctaaactattgaaa
atgaaaataaaataatataaaatgaatcatagtgcaagagatacttgccagaggatgaatattttactgcattcatgctttatggc
agctaatagaggcattaaattaaattttaatttacaataggaggcgatattaatgaactttaataaaattgatttagacaattgga
agagaaaagagatatttaatcattatttgaaccaacaaacgacttttagtataaccacagaaattgatattagtgttttataccga
aacataaaacaagaaggatataaatttacctgcatttatttcttagtgacaagggtgataaactcaaatacagcttttagaac
tggttacaatagcgacggagagttaggttatgggataagttagagccactttataccaattttgatggtgtatctaaaacattct
ctggtatttggactcctgtaaagaatgacttcaaagagttttatgatttatacctttctgatgtagagaaatataatggttcgggg
aaattgtttcccaaaacacctatacctgaaaatgcttttctctttctattattccatggacttcatttactgggtttaacttaaa
tatcaataataatagtaattaccttctacccattattacagcaggaaaattcattaataaaggtaattcaatatatttaccgctat
ctttacaggtacatcattctgtttgtgatggttatcatgcaggattgtttatgaactctattcaggaattgtcagataggcctaat
gactggcttttataataaggaggtcgacgtcatgtttattgatacattaattgaaaagattagagaaaaggataatccttccgtt
gtaggattagaccctaaaattgaatatgttccgtctttataaaggaagacatgtataaaaaatacgggaaaaatttaaaagctgt
ggcagaggcgattctcctcttcaataaatatattattgatgcggtttacgatattgttcctgcagtaaaaccgcagcttgcatatt
atgaaatgtacggccttgaaggcatgagggtgttttatgaaacttgcaaatatgcaaaggaaaaaggactttggttattgcagac
ggaaaaagaaacgacataggttccaccgcccagtgttattctgccgcatatcttggaaaaacggacattgatgaaggtataagcga
ggcggttttgatgtggatgccctgacagtcaaccgtatcttggtgtggacggtattaagccttttatagatgactgtgtcaagt
acaacaagggcatatttgttctggtcaagacatcaaacaagtcatccggagaaattcaggacatactcacccaggaaggaagaagc
atttatgagattgttgcggagtatgttgaatcatggggtgaaaacaaaaaaggaaaatatggatacagttgtgtgggagcagtggt
tggagcaacttatcccaatctggccaaaattttaagaaagattctgaaaaattcctatataccggttccgggctatggagctcagg
gaggaacagccagagatgtagcccattgctttaattatgacgggctcggagcaattgtcaatgcatcaagaagcataatgtgtgcc
tacaaatctgaacaatggaagaatgtttacagcgaagaaaagtttatgaggcatcaagagccgaggcaataagaatgagggacga
tattaacagtgcgttgcgagacaggaagtaagccgggcctcgagaaaacaaaaggctcagtcggaagactgggcctttgttttg
gtaccgaattcggcgcgcctcagcgttt
```

Figure 5A (continued)

E50A protein sequence (1 - 873, change at 553, G -> R) (SEQ ID NO: 6)

MTKIANKYEVIDNVEKLEKALKRLREAQSVYATYTQEQVDKIFFEAAMAANKMRIPLAKM
AVEETGMGVVEDKVIKNHYASEYIYNAYKNTKTCGVIEEDPAFGIKKIAEPLGVIAAVIP
TTNPTSTAIFKTLIALKTRNAIISPHPRAKNSTIEAAKIVLEAAVKAGAPEGIIGWIDV
PSLELTNLVMREADVILATGGPGLVKAAYSSGKPAIGVGAGNTPAIIDDSADIVLAVNSI
IHSKTFDNGMICASEQSVIVLDGVYKEVKKEFEKRGCYFLNEDETEKVRKTIIINGALNA
KIVGQKAHTIANLAGFEVPETTKILIGEVTSVDISEEFAHEKLCPVLAMYRAKDFDDALD
KAERLVADGGFGHTSSLYIDTVTQKEKLQKFSERMKTCRILVNTPSSQGGIGDLYNFKLA
PSLTLGCGSWGGNSVSDNVGVKHLLNIKTVAERRENMLWFRTPEKIYIKRGCLPVALDEL
KNVMGKKKAFIVTDNFLYNNGYTKPITDKLDEMGIVHKTFFDVSPDPSLASAKAGAAEML
AFQPDTIIAVGGRSAMDAAKIMWVMYEHPEVDFMDMAMRFMDIRKRVYTFPKMGQKAYFI
AIPTSAGTGSEVTPFAVITDEKTGIKYPLADYELLPDMAIVDADMMMNAPKGLTAASGID
ALTHALEAYVSMLATDYTDSLALRAIKMIFEYLPRAYENGASDPVAREKMANAATIAGMA
FANAFLGVCHSMAHKLGAFYHLPHGVANALMINEVIRFNSSEAPTKMGTFPQYDHPRTLE
RYAEIADYIGLKGKNNEEKVENLIKAIDELKEKVGIRKTIKDYDIDEKEFLDRLDEMVEQ
AFDDQCTGTNPRYPLMNEIRQMYLNAYYGGAKK

E50C protein sequence (1 - 873, change at 494, D -> G) (SEQ ID NO: 7)

MTKIANKYEVIDNVEKLEKALKRLREAQSVYATYTQEQVDKIFFEAAMAANKMRIPLAKM
AVEETGMGVVEDKVIKNHYASEYIYNAYKNTKTCGVIEEDPAFGIKKIAEPLGVIAAVIP
TTNPTSTAIFKTLIALKTRNAIISPHPRAKNSTIEAAKIVLEAAVKAGAPEGIIGWIDV
PSLELTNLVMREADVILATGGPGLVKAAYSSGKPAIGVGAGNTPAIIDDSADIVLAVNSI
IHSKTFDNGMICASEQSVIVLDGVYKEVKKEFEKRGCYFLNEDETEKVRKTIIINGALNA
KIVGQKAHTIANLAGFEVPETTKILIGEVTSVDISEEFAHEKLCPVLAMYRAKDFDDALD
KAERLVADGGFGHTSSLYIDTVTQKEKLQKFSERMKTCRILVNTPSSQGGIGDLYNFKLA
PSLTLGCGSWGGNSVSDNVGVKHLLNIKTVAERRENMLWFRTPEKIYIKRGCLPVALDEL
KNVMGKKKAFIVTGNFLYNNGYTKPITDKLDEMGIVHKTFFDVSPDPSLASAKAGAAEML
AFQPDTIIAVGGGSAMDAAKIMWVMYEHPEVDFMDMAMRFMDIRKRVYTFPKMGQKAYFI
AIPTSAGTGSEVTPFAVITDEKTGIKYPLADYELLPDMAIVDADMMMNAPKGLTAASGID
ALTHALEAYVSMLATDYTDSLALRAIKMIFEYLPRAYENGASDPVAREKMANAATIAGMA
FANAFLGVCHSMAHKLGAFYHLPHGVANALMINEVIRFNSSEAPTKMGTFPQYDHPRTLE
RYAEIADYIGLKGKNNEEKVENLIKAIDELKEKVGIRKTIKDYDIDEKEFLDRLDEMVEQ
AFDDQCTGTNPRYPLMNEIRQMYLNAYYGGAKK

Figure 10

E50A Cthe_0423 nucleotide sequence (531351 - 533972, change at 533007, G -> A) (SEQ ID NO: 8)

```
ATGACGAAAATAGCGAATAAATACGAAGTTATTGATAATGTTGAAAAGCTTGAAAAGGCTTTGAAACGTTTAAG
AGAAGCTCAAAGTGTTTATGCAACCTATACACAGGAGCAGGTTGACAAAATTTCTTTGAGGCGGCAATGGCGG
CCAATAAAATGAGAATTCCTCTTGCCAAAATGGCTGTGGAGGAAACAGGCATGGGAGTGGTTGAAGACAAGGTT
ATCAAAAACCACTATGCTTCTGAGTATATCTATAATGCGTACAAAAACACTAAAACCTGCGGTGTTATTGAAGA
GGACCCTGCTTTCGGTATTAAAAAAATAGCAGAGCCTTTGGGGGTTATTGCGGCGGTTATACCTACTACGAATC
CGACATCGACAGCAATCTTTAAGACTCTTATTGCATTAAAGACGAGAAATGCAATTATTATAAGCCCACACCCC
AGGGCAAAAAACTCAACGATAGAAGCGGCGAAAATTGTTTTGGAGGCGGCCGTTAAAGCCGGTGCTCCGGAAGG
CATCATTGGCTGGATTGATGTGCCGAGCCTTGAACTTACCAACCTGGTAATGAGAGAAGCAGATGTGATTCTCG
CAACAGGCCGTCCCGGACTGGTTAAAGCAGCTTACTCTTCGGGCAAACCGGCTATTGGTGTCGGAGCGGGCAAT
ACTCCTGCAATTATTCATGATTCGCCCGACATTGTCTTGGCAGTGAACTCAATAATACATTCAAAAACTTTCGA
CAACGGTATGATTTGTGCTTCAGAGCAATCGGTCATTGTTCTGGACGGGTATATAAAGAGGTAAAAAAAGAAT
TTGAAAAAGAGGATGCTATTTCTTAAATGAAGATGAAACTGAAAAGGTAAGAAAAACAATTATAATAAACGGT
GCGTTAAATGCCAAGATAGTAGGTCAGAAAGCTCACACAATTGCAAACCTTGCAGGTTTTGAGGTACCCGAGAC
TACAAAAATTCTGATAGGCGAAGTTACCAGCGTGGATATTTCCGAAGAATTTGCCCACGAAAAGTTGTGCCCGG
TACTGGCAATGTACAGGGCAAAGGATTTTGACGATGCCCTTGATAAAGCAGAAAGGTTGGTAGCTGACGGTGGA
TTTCGCCATACTTCGTCACTTTATATAGATACGGTAACACAGAAACAGAAACTTCAGAAATTCTCTGAAAGCAT
GAAAACCTGCCGTATATTGGTTAATACGCCGTCATCCCAGGGAGGTATCGGTGACCTTTACAACTTCAAGCTTG
CTCCGTCTCTCACCCTCGGCTGCGGTTCCTGGGGAGGAAATTCAGTTTCCGACAATGTGGGAGTCAAGCATTTG
TTAAACATTAAAACAGTTGCCGAGAGGAGAGAGAACATGCTCTGGTTCAGAACACCTGAAAAGATTTATATAAA
AAGAGGTTGTCTGCCTGTTGCATTGGATGAGCTTAAAAATGTAATGGGTAAAAAGAAAGCATTTATTGTAACGG
ATAACTTCCTGTACAATAACGGCTACACCAAGCCGATTACGGATAAGCTGGATGAAATGGGAATTGTGCACAAG
ACCTTCTTTGATGTGTCTCCAGACCCATCCCTTGCATCTGCCAAAGCCGGTGCGGCAGAAATGCTGGCTTTCCA
GCCTGACACCATAATTGCGGTCGGCGGCAGATCTGCCATGGACGCCGCCAAAATCATGTGGGTGATGTATGAAC
ATCCGGAAGTTGACTTTATGGACATGGCAATGAGATTTATGGATATAAGAAAGAGAGTTTACACCTTCCCGAAG
ATGGGACAGAAGGCATACTTTATCGCAATTCCGACTTCCGGGTACAGGTTCAGAAGTGACACCTTTTGCGGT
TATTACTGATGAAAAACAGGAATTAAATACCCTCTGGCCGACTATGAATTGTTGCCGGACATGGCTATTGTAG
ATGCCGATATGATGATGAATGCTCCAAAGGGACTTACCGCAGCTTCCGGTATAGACGCATTGACCCACGCTCTG
GAAGCCTATGTTTCAATGCTTGCGACCGACTATACGGATAGCCTTGCCCTTCGTGCAATAAAGATGATATTTGA
ATATCTCCCGAGAGCCTATGAAAACGGTGCAAGTGACCCGGTTGCAAGAGAGAAAATGGCCAATGCCGCAACAA
TAGCCCGGAATGGCTTTTCCCAATGCCTTTTTCGGTGTATGCCATTCAATGGCGCACAAACTGGGTGCTTTTTAT
CACCTGCCCCACGGTGTTGCCAATGCACTTATGATAAACGAAGTAATCAGATTCAACTCATCCGAGGCTCCGAC
CAAGATGGGTACTTTCCCGCAGTATGACCATCCGCGCACGCTGGAAAGGTATGCAGAAATTGCCGATTATATCG
GACTTAAGGGCAAGAATAACGAAGAAAAGTTGAAAACTTGATTAAAGCTATTGATGAGCTTAAAGAAAAGGTG
GGCATCAGGAAGACCATCAAAGATTATGACATAGATGAAAAGGAATTTTTGGACAGACTGGACGAAATGGTGGA
ACAGGCTTTTGACGACCAGTGCACAGGTACAAATCCAAGATACCCGCTTATGAATGAAATCAGGCAAATGTATC
TGAACGCTTATTACGGAGGTGCGAAGAAATGA
```

Figure 11a

E50C Cthe_0423 nucleotide sequence (531351 - 533972, change at 532831, A -> G) (SEQ ID NO: 9)

```
ATGACGAAAATAGCGAATAAATACGAAGTTATTGATAATGTTGAAAAGCTTGAAAAGGCTTTGAAACGTTTAAG
AGAAGCTCAAAGTGTTTATGCAACCTATACACAGGAGCAGGTTGACAAAATTTTCTTTGAGGCGGCAATGGCGG
CCAATAAAATGAGAATTCCTCTTGCCAAAATGGCTGTGGAGGAAACAGGCATGGGAGTGGTTGAAGACAAGGTT
ATCAAAAACCACTATGCTTCTGAGTATATCTATAATGCGTACAAAAACACTAAAACCTGCGGTGTTATTGAAGA
GGACCCTGCTTTCGGTATTAAAAAAATAGCAGAGCCTTTGGGGGTTATTGCGGCGGTTATACCTACTACGAATC
CGACATCGACAGCAATCTTTAAGACTCTTATTGCATTAAAGACGAGAAATGCAATTATTATAAGCCCACACCCC
AGGGCAAAAAACTCAACGATAGAAGCGGCGAAAATTGTTTTGGAGGCGGCCGTTAAAGCCGGTGCTCCGGAAGG
CATCATTGGCTGGATTGATGTGCCGAGCCTTGAACTTACCAACCTGGTAATGAGAGAAGCAGATGTGATTCTCG
CAACAGGCGGTCCCGGACTGGTTAAAGCAGCTTACTCTTCGGGCAAACCGGCTATTGGTGTCGGAGCGGGCAAT
ACTCCTGCAATTATTGATGATTCGGCCGACATTGTCTTGGCAGTGAACTCAATAATACATTCAAAAACTTTCGA
CAACCGTATGATTTGTGCTTCAGAGCAATCGGTCATTGTCTCGACGGCGTATATAAAGAGGTAAAAAAAGCAAT
TTGAAAAAGAGGATGCTATTTCTTAAATCAAGATGAAACTGAAAAGGTAAGAAAAACAATTATAATAAACGGT
GCGTTAAATGCCAAGATAGTAGGTCAGAAAGCTCACACAATTGCAAACCTTGCAGGTTTTGAGGTACCCGAGAC
TACAAAAATTCTGATAGGCGAAGTTACCAGCGTGGATATTTCCGAAGAATTTGCCCACGAAAAGTTGTGCCCGG
TACTGGCAATGTACAGGGCAAAGGATTTTGACGATGCCCTTGATAAAGCAGAAAGGTTGGTAGCTGACGGTGGA
TTTGGCCATACTTCGTCACTTTATATAGATACGGTAACACAGAAAGAGAAACTTCAGAAATTCTCTGAAAGGAT
GAAAACCTGCCGTATATTGGTTAATACGCCGTCATCCCAGGGAGGTATCGGTGACCTTTACAACTTCAAGCTTG
CTCCGTCTCTCACCCTCGGCTGCGGTTCCTGGGGAGGAAATTCAGTTTCCGACAATGTGGGAGTCAAGCATTTG
TTAAACATTAAAACAGTTGCCGAGAGGAGAGAGAACATGCTCTGGTTCAGAACACCTGAAAAGATTTATATAAA
AAGAGGTTGTCTGCCTGTTGCATTGGATGAGCTTAAAAATGTAATGGGTAAAAGAAAGCATTTATTGTAACG**G
GT**AACTTCCTGTACAATAACGGCTACACCAAGCCGATTACGGATAAGCTGGATGAAATGGGAATTGTGCACAAG
ACCTTCTTTGATGTGTCTCCAGACCCATCCCTTGCATCTGCCAAAGCCGGTGCGGCAGAAATGCTGGCTTTCCA
GCCTGACACCATAATTGCGGTCGGCGGCGGATCTGCCATGGACGCGGCCAAAATCATGTGGGTGATGTATGAAC
ATCCCGAAGTTGACTTTATGCACATGCCAATGACATTTATGGATATAACAAACAGAGTTTACACCTTCCCGAAG
ATGGCACAGAAGGCATACTTTATCGCAATTCCGACTTCCCCGCGGTACACGTTCAGAAGTGACACCTTTGCCGT
TATTACTGATGAAAAAACAGGAATTAAATACCCTCTGGCCGACTATGAATTGTTGCCGGACATGGCTATTGTAG
ATGCCGATATGATGATGAATGCTCCAAAGGGACTTACCGCAGCTTCCGGTATAGACGCATTGACCCACGCTCTG
GAAGCCTATGTTTCAATGCTTGCGACCGACTATACGGATAGCCTTGCCCTTCGTGCAATAAAGATGATATTTGA
ATATCTCCCGAGAGCCTATGAAAACGGTGCAAGTGACCCGGTTGCAAGAGAGAAAATGGCCAATGCCGCAACAA
TAGCCGGAATGGCTTTTGCCAATGCCTTTTGGGTGTATGCCATTCAATGGCGCACAAACTGGGTGCTTTTTAT
CACCTGCCCCACGGTGTTGCCAATGCACTTATGATAAACGAAGTAATCAGATTCAACTCATCCGAGGCTCCGAC
CAAGATGGGTACTTTCCCGCAGTATGACCATCCGCGCACGCTGGAAAGGTATGCAGAAATGCCGATTATATCG
GACTTAAGGGCAAGAATAACGAAGAAAAAGTTGAAAACTTGATTAAAGCTATTGATGAGCTTAAAGAAAAGGTG
GGCATCAGGAAGACCATCAAAGATTATGACATAGATGAAAAGGAATTTTTGGACAGACTGGACGAAATGGTGGA
ACAGGCTTTTGACGACCAGTGCACAGGTACAAATCCAAGATACCCGCTTATGAATGAAATCAGGCAAATGTATC
TGAACGCTTATTACGGAGGTGCGAAGAAATGA
```

Figure 11b ns. In particular, the invention relates
NUCLEIC ACID MOLECULES CONFERRING ENHANCED ETHANOL TOLERANCE AND MICROORGANISMS HAVING ENHANCED TOLERANCE TO ETHANOL This application claims priority to U.S. provisional application 61/346,660, filed May 20, 2010, which is incorporated herein in its entirety.

This invention was made with government support under Contract Number DE-AC05-00OR22725 between the United States Department of Energy and UT-Battelle, LLC. The U.S. Government has certain rights in this invention.

FIELD OF THE INVENTION

This invention generally relates to the field of genetic engineering of microorganisms. In particular, the invention relates to isolated nucleic acid molecules that confer enhanced tolerance to ethanol and to genetically engineered microorganisms that display enhanced tolerance to ethanol as a result of expression of such nucleic acid molecules. The genetically engineered microorganisms are advantageous for use in fermentation of biomass materials to produce biofuels.

BACKGROUND OF THE INVENTION

Biomass-based bioenergy is crucial to meet the goal of making cellulosic biofuels cost-competitive with gasoline. Lignocellulosic materials represent an abundant feedstock for cellulosic-biofuel production. A core challenge in converting cellulosic material to biofuels such as ethanol and butanol is the recalcitrance of biomass to breakdown. Because of the complex structure of lignocellulosic biomass, pretreatment is necessary to make it accessible for enzymatic attack. Severe biomass pretreatments are required to release the sugars, which along with by-products of fermentation can create inhibitors in the production of ethanol or butanol, for example. During the pretreatment processes, a range of inhibitory chemicals are formed that include sugar degradation products such as furfural and hydroxymethyl furfural (HMF); weak acids such as acetic, formic, and levulinic acids; lignin degradation products such as the substituted phenolics vanillin and lignin monomers. In addition, the metabolic byproducts such as ethanol, lactate, and acetate also impact the fermentation by slowing and potentially stopping the fermentation prematurely. The increased lag phase and slower growth increases the ethanol cost due to both ethanol production rate and total ethanol yield decreases.

Efficient conversion of lignocellulosic hydrolysates to biofuel requires high-yield production and resistance to industrially relevant stresses and inhibitors. To overcome the issue of inhibition caused by pretreatment processes, there are two approaches, one is to remove the inhibitor after pretreatment from the biomass physically or chemically, which requires extra equipment and time leading to increased costs. A second approach utilizes inhibitor tolerant microorganisms for efficient fermentation of lignocellulosic material to ethanol (Almeida et al., *Journal of Chemical Technology and Biotechnology* 82, 340-349, 2007).

Two different genes have been identified recently that confer enhanced tolerance to pretreatment inhibitors (Yang et al., *Proc. Natl. Acad. Sci. USA* 107:10395-400, 2010; Yang et al., *BMC Microbiology* 10:135, 2010). Microbial ethanol tolerance has been thought to be a complex and likely a multigenic trait (Williams et al., *Appl. Microbiol. Biotechnol.* 74: 422-432, 2007; Timmons et al., *Appl. Microbiol. Biotechnol.* 82: 929-939, 2009). As reviewed by Stephanopoulos (*Science* 315: 801-804, 2007), there has been accumulating evidence that no single gene can endow microbes with tolerance to ethanol and other toxic compounds. To date, little progress has been made in identification of key genetic changes that confer enhanced ethanol tolerance. Global transcription machinery engineering (gTME) is an approach that has improved glucose/ethanol tolerance in *Saccharomyces cerevisiae* and led to increased productivity (Alper et al., *Science* 314, 1565-1568, 2006). See also U.S. Published Application 2007/0072194 A1.

In prokaryotic systems, there is increasing evidence for the link between alcohol dehydrogenases and maintenance of cellular redox-balance under ethanol stress conditions. For example, an ethanol adapted strain 39EA of *Thermoanaerobacter ethanolicus* (formerly *Clostridium thermohydrosulfuricum*) was found to lack detectable levels of NAD-linked ADH activity as compared to the wild-type strain (Lovitt, R. W. et al., 1988. Ethanol-production by thermophilic bacteria-biochemical basis for ethanol and hydrogen tolerance in *Clostridium thermohydrosulfuricum*. J. Bacteriol. 170:2809-2815). Similarly, *T. ethanolicus* strain 39E H8 adapted to high ethanol levels also lacked activity for the primary alcohol dehydrogenase that is involved in nicotinamide co-factor recycling while increasing the percentage of transmembrane fatty acids (Burdette, D. S. et al., 2002. Physiological function of alcohol dehydrogenases and long-chain ($C_{30}$) fatty acids in alcohol tolerance of *Thermoanaerobacter ethanolicus*. Appl. Environ. Microbiol. 68:1914-1918). Thus, mutations in alcohol dehydrogenase genes and redox balance may be beneficial for adaptation to elevated ethanol levels in bacterial strains.

Bacterial systems such as *Thermoanaerobacter ethanolicus* contain primary and secondary alcohol dehydrogenases with differing co-factor specificities. In *C. thermocellum*, conflicting biochemical studies suggest that the alcohol dehydroganses are either NADH-specific (15) or capable of utilizing NADH or NADPH (24). Among four Fe-containing alcohol dehydrogenases in *C. thermocellum*, Cthe0423, a bi-functional aldehyde/alcohol dehydrogenase, is the third most abundant transcript in the cell, while the other alcohol dehydrogenases are transcribed in much lower abundance (6), suggesting that Cthe0423 is the main ethanol dehydrogenase in *C. thermocellum*.

SUMMARY OF THE INVENTION

The present invention has identified that mutations associated with a single gene can endow a microorganism with enhanced tolerance to ethanol. More specifically, it has been identified that mutations within the acetaldehyde-CoA/alcohol dehydrogenase gene confer enhanced tolerance to ethanol. Redox chemistry and co-factor specificity are identified as important factors in enhancing ethanol tolerance. Accordingly, the present invention provides isolated nucleic acids capable of conferring an ethanol resistance phenotype, related expression vectors, genetically engineered microorganisms having enhanced tolerance to ethanol, as well as methods of making and using such genetically modified microorganisms for production of biofuels based on fermentation of biomass materials.

In one aspect, the present invention is directed to isolated nucleic acid molecules encoding a mutant acetaldehyde-CoA/alcohol dehydrogenase and capable of conferring enhanced ethanol tolerance to a microorganism.

In some embodiments, the nucleic acid molecule contains one or more nucleotide changes relative to the wild type (native) nucleic acid molecule, which result in a substitution, insertion or deletion of one or more amino acids in the alcohol dehydrogenase domain of the protein.

In specific embodiments, the one or more nucleotide changes result in an alteration of one or more amino acids that constitute the active site of the alcohol dehydrogenase domain.

In other specific embodiments, the isolated nucleic acid molecule encodes a mutant acetaldehyde-CoA/alcohol dehydrogenase, wherein the mutant protein differs from the wild type protein by a substitution or deletion of a residue that is highly conserved among bacterial species. Examples of conserved residues include H at positions 730 and 734 of Cthe_0423 (SEQ ID NO: 1) or the corresponding positions of a Cthe_0423 homolog. These two positions are also part of the active site of the alcohol dehydrogenase domain. An example of a substitution is the substitution of H with R at position 734.

In other specific embodiments, the isolated nucleic acid molecule encodes a mutant acetaldehyde-CoA/alcohol dehydrogenase wherein the mutant protein differs from the wild type protein by a substitution or deletion of a residue that is not conserved among bacterial species. An example of such mutant protein is a mutant Cthe_0423 protein with a substitution of P with L at position 704.

In still other embodiments, the isolated nucleic acid molecule encodes a mutant acetaldehyde-CoA/alcohol dehydrogenase wherein the mutant protein differs from the wild type protein by several (i.e., two or more) substitutions of amino acids, for example, the mutant Cthe_0423 protein as set forth in SEQ ID NO: 2 (double mutant H734R and P704L).

In other embodiments, the present invention provides isolated nucleic acid molecules which encode a mutant acetaldehyde-CoA/alcohol dehydrogenase containing only the alcohol dehydrogenase domain of the native protein without the acetaldehyde-CoA dehydrogenase domain, having one or more amino acid substitutions at positions described (e.g., conserved residues or residues that define the active site). In alternative embodiments, the invention provides nucleic acid molecules encoding a mutant alcohol dehydrogenase having one or more amino acid substitutions at positions that align with positions described for a bi-functional acetaldehyde-CoA/alcohol dehydrogenase.

In another aspect, the present invention provides expression vectors which contain an isolated nucleic acid molecule described herein for expression of a mutant acetaldehyde-CoA/alcohol dehydrogenase or mutant alcohol dehydrogenase in a microbial host.

In a further aspect, the present invention provides microorganisms which are genetically engineered to express a mutant acetaldehyde-CoA/alcohol dehydrogenase or mutant alcohol dehydrogenase and display enhanced ethanol tolerance.

Microorganisms encompassed within the scope of the present invention include both bacteria and fungi. Examples of bacterial strains of interest include *Acetobacterium, Bacillus, Streptococcus, Clostridium* (e.g., *C. thermocellum*), *Anaerocellum* (e.g., *Anaerocellum thermophilum*), *Caldicellulosiruptor* (e.g., *C. saccharolyticus*), and *Thermoanaerobacter* (e.g., *Thermoanaerobacter* sp. X514), *Zymomonas* sp. (e.g., *Z. mobilis*), *E. coli*, *Gluconobacter* sp. (e.g., *Gluconobacter oxydans*, previously known as *Acetobacter suboxydans*), and Green sulfur and Green non-sulfur bacteria. Examples of fungal strains contemplated by the present invention include *Saccharomyces* sp., *Kluyveromyces* sp., *Pichia* sp., *Candida* sp., and *Schizosaccharomycetes* sp.

In some embodiments, the nucleic acid molecule on the expression vector that encodes a mutant protein is derived from the endogenous wild type gene from the microorganism receiving the expression vector. In other embodiments, the nucleic acid molecule on the expression vector that encodes the mutant protein is heterologous to the microbial recipient of the expression vector.

In still another aspect, the invention is directed to methods of genetically engineering microorganism with enhanced ethanol tolerance. Such microorganisms can be generated, e.g., by introducing to a microbial strain an expression vector that directs the expression of a mutant acetaldehyde-CoA/alcohol dehydrogenase or mutant alcohol dehydrogenase as described herein. Alternatively, such microorganisms can be generated by specifically targeting the gene within the microorganisms for mutagenesis which codes for acetaldehyde-CoA/alcohol dehydrogenase (AdhE gene) or for alcohol dehydrogenase, e.g., by altering an AdhE gene at positions that align with codons for H734, P704, G553, or D494 of SEQ ID NO: 1.

The genetically modified microorganisms that display enhanced tolerance to ethanol can be additionally modified as appropriate, for example, by transformation with additional recombinant genes or sequences suitable for fermentation and production of ethanol.

In a further aspect, the present invent provides a method of producing biofuels from cellulosic biomass based on use of the microbial strains described herein.

BRIEF DESCRIPTION OF THE DRAWINGS

FIGS. 2A-2C. Wild type and mutant Cthe_0423 protein (acetaldehyde-CoA/alcohol dehydrogenase) nucleotide and amino acid sequences. The amino acid residues at positions 704 and 734 (mutation sites) of the wild type Cthe_0423 protein (SEQ ID NO: 1) are indicated in larger font size. Amino acids 17-453, which define the ALDH domain, are shown in bold. Within the ADH domain (amino acids 463-864), the 4 metal binding sites are in lower cases, bold and underlined. These four metal binding sites are also part of the active site. The remaining 14 amino acids of the active site are shown in italics, bold and underlined.

FIG. 3. Domain and motif sites of *C. thermocellum* AdhE (Cthe_0423) protein.

FIGS. 4A-4E. Mutant *C. thermocellum* alcohol dehydrogenase confers enhanced ethanol tolerance upon introduction into the *C. thermocellum* DSM 1313 wild-type background.

FIGS. 5A-5B. Sequence and map of plasmid pAMG205.

FIG. 10. Mutant E50A and E50C protein (acetaldehyde-CoA/alcohol dehydrogenase) amino acid sequences.

FIG. 11. Mutant E50A and E50C (acetaldehyde-CoA/alcohol dehydrogenase) nucleotide sequences.

DETAILED DESCRIPTION OF THE INVENTION

Figure 1:
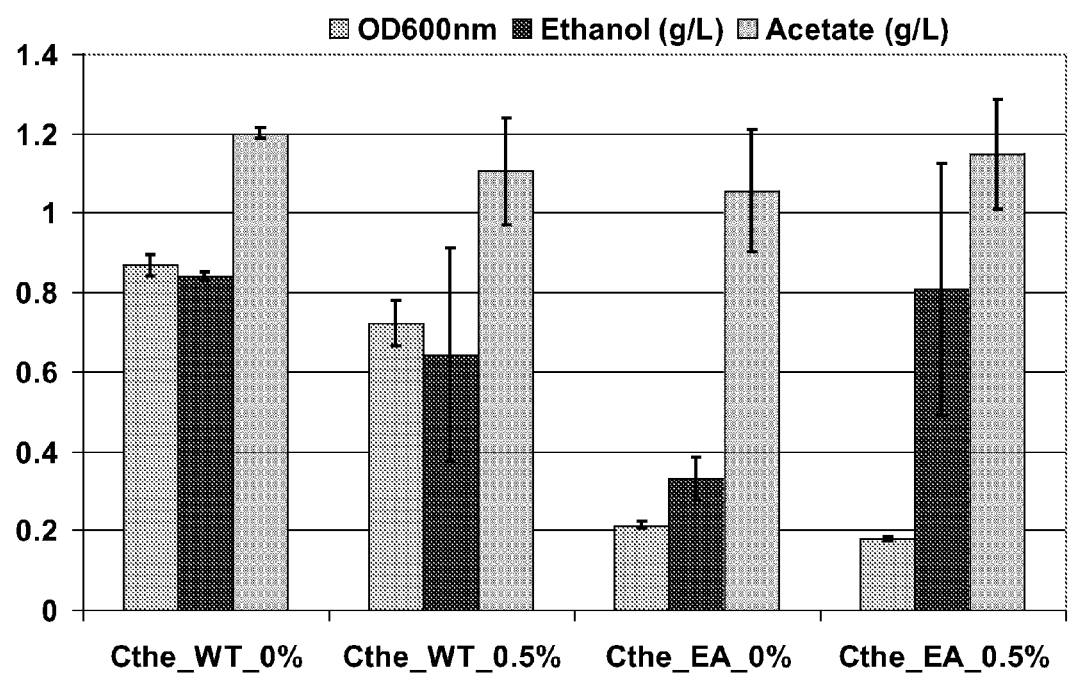
FIG. 1. Net ethanol and acetate production from the wild type *C. thermocellum* strain (Cthe_WT) and a mutant ethanol tolerant *C. thermocellum* strain (Cthe_EA) with added (0.5%) ethanol or without added ethanol (0%).

In accordance with the present invention, mutations within a single gene, namely, the gene coding for acetaldehyde-CoA/alcohol dehydrogenase, have been identified as dictating enhanced tolerance to ethanol.

Accordingly, in one aspect, the invention provides isolated nucleic acid molecules encoding a mutant acetaldehyde-CoA/alcohol dehydrogenase and capable of conferring enhanced ethanol tolerance to a microorganism.

In some embodiments, the isolated nucleic acid molecules encoding a mutant acetaldehyde-CoA/alcohol dehydrogenase are derived from a wild type (i.e., naturally occurring) acetaldehyde-CoA/alcohol dehydrogenase-encoding gene of a bacterial species, including both Gram-negative and Gram positive bacterial. Examples of bacteria of particular interest include species of *Acetobacterium, Bacillus, Enterobacteriaceae, Streptococcus, Clostridium, Zymomonas*, and *Gluconobacter*. In specific embodiments, the isolated nucleic acids are derived from *Clostridium themocellum, Clostridium phytofermentans, Clostridium cellulolyticum, Clostridium beijerinckii, Clostridium cellulovorans, Thermoanaerobacterium saccharolyticum, Z. mobilis* and *E. coli*.

In other embodiments, the isolated nucleic acid molecules encoding a mutant acetaldehyde-CoA/alcohol dehydrogenase are derived from a wild type (i.e., naturally occurring) acetaldehyde-CoA/alcohol dehydrogenase-encoding gene of a fungal species. Examples of fungi include *Saccharomyces* sp. (e.g., *S. cerevisiae*), *Kluyveromyces* sp., *Pichia* sp. (e.g., *Pichia pastoris*), *Candida* sp., and *Schizosaccharomycetes* sp.

In one specific embodiment, the invention provides an isolated nucleic acid molecule derived from *Clostridium thermocellum*, which encodes a mutant acetaldehyde-CoA/alcohol dehydrogenase. The wild type acetaldehyde-CoA/alcohol dehydrogenase from *Clostridium thermocellum*, also referred to herein as the "Cthe_0423 protein" or "ADHE" (SEQ ID NO: 1), is a bi-functional protein of 873 amino acids involved in pyruvate metabolism. This enzyme utilizes NADP and iron as co-factors, and contains two conserved domains, namely, an acetaldehyde dehydrogenase (ALDH) superfamily domain at the N-terminal portion of the protein, and an iron-binding alcohol dehydrogenase (ADH) superfamily domain at the C-terminal portion of the protein (see FIG. 3). Within the C-terminal alcohol dehydrogenase domain, there are 18 putative active site residues, 4 of which are metal binding sites (see FIG. 3 showing site features).

The acetaldehyde-CoA/alcohol dehydrogenase is conserved among different kingdoms of archaea, prokaryotes, and eukaryotes. A BLAST search using the Cthe_0423 protein (SEQ ID NO: 1) has revealed that the top 500 homologs have greater than 96% length coverage of the Cthe_0423 protein, an E-value of 0, and with significant sequence identities with the Cthe_0423 protein, ranging from *Psychromonas ingrahamii* 37 (58% identity) to *Elusimicrobium minutum* Pei191 (80% identity). Homologs of the Cthe_0423 protein are also present in other microorganisms suitable for use in the production of biofuels from cellulosic biomass such as *E. coli* (about 60% identity), *C. phytofermentans* (77% identity), *Clostridium cellulolyticum* (75% identity), *Clostridium beijerinckii* (67% identity), *Clostridium cellulovorans* (66% identity), and *Thermoanaerobacterium saccharolyticum* (52% identity).

By "Cthe_0423 homolog proteins" it refers to proteins having a sequence identity of at least 40%, 45%, 50%, 55%, 60%, 65%, 70%, 75%, 80%, 85%, 90%, 95% or greater over the length of the Cthe_0423 protein (SEQ ID NO: 1), and having a two-domain structure: an acetaldehyde dehydrogenase (ALDH) superfamily domain at the N-terminal portion, and an iron-binding alcohol dehydrogenase (ADH) superfamily domain at the C-terminal portion. Given the specific amino acid sequence of a protein of interest, those skilled in the art can determine the portions of the protein representing an ALDH domain and an ADH domain, respectively. For example, using the sequence of the Cthe_0423 protein (SEQ ID NO: 1) as the query sequence, a search in the Conserved Domain Database (CDD), available at the web server of National Center for Biotechnology Information (NCBI), has identified that amino acids 17-453 of this protein define a domain that shares significant homologies with other members of the ALDH superfamily (e.g., matching cd07122 with a 50% sequence identity); and amino acids 463-864 define a domain that shares significant homologies with other members of the iron-binding ADH superfamily (e.g., matching cd08178 with a 46% sequence identity). See FIG. 3. Expect Value with threshold of 0.01 and low-complexity filter have been applied in this search in the database of CDD-37014PSSMs. Alternatively, one can use the ALDH and ADH domains of the Cthe_0423 protein as the basis for comparison of sequences and determination of domain structures of a protein of interest. For example, an amino acid sequence is considered herein to define an ADH domain if such amino acid sequence shares at least 20%, 25%, 30%, 35%, 40%, 45%, 50%, 55%, 60%, 65%, 70%, 75%, 80%, 85%, 90%, 95% or greater identity, with amino acids 463-864 of SEQ ID NO: 1.

The wild type acetaldehyde-CoA/alcohol dehydrogenase has been shown in *E. coli*, grown under anaerobic or fermentative conditions, to catalyze the sequential reduction of acetyl-CoA to acetaldehyde and then to ethanol. Acetyl-CoA is first converted into an enzyme-bound thiohemiacetal by the N-terminal acetaldehyde dehydrogenase domain, which is subsequently reduced to ethanol by the C-terminal $NAD^+$-dependent alcohol dehydrogenase domain. Nnyepi et al., *Archives of Biochemistry and Biophysics, Volume* 459, Issue 1, Pages 1-9 (2007).

Nucleic acid molecules encoding a mutant acetaldehyde-CoA/alcohol dehydrogenase that confers an enhanced ethanol tolerance phenotype can be created from a wild type acetaldehyde-CoA/alcohol dehydrogenase-encoding gene by genetic engineering, e.g., site-specific or random mutagenesis.

In some embodiments, the mutant nucleic acid molecule is engineered to include one or more nucleotide changes which result in a substitution, insertion or deletion of one or more amino acids in the alcohol dehydrogenase domain of the protein.

In certain embodiments, the nucleotide change(s) result in an alteration (such as substitution or deletion) of one or more amino acids that are part of the active site of the ADH domain. By "active site" it is meant a site within an enzyme that binds the substrate and/or catalyzes a reaction to produce a product. An active site of an enzyme is typically formed by multiple amino acid residues, which may not be adjacent to each other in the primary structure (sequence) of the protein. The eighteen amino acid residues that constitute the active site of the ADH domain of the Cthe_0423 protein, including four iron-binding residues, are shown in FIG. 2A. Those skilled in the art will be able to identify the amino acid residues that define the active site of a Cthe_0423 homolog by aligning the sequences of the Cthe_0423 protein and the homolog protein.

In other embodiments, the isolated nucleic acid molecule encodes a mutant acetaldehyde-CoA/alcohol dehydrogenase, wherein the mutant protein differs from the wild type protein by a substitution or deletion of a residue that is highly conserved among species, e.g., among bacterial and fungal species, among bacterial species, or among a subgenus of bacterial species (such as *Clostridium* species). Examples of conserved residues include "H" at position 734 of SEQ ID NO: 1 (conserved among species including *E. coli, Clostridium* sp., and *S. cerevisiae*); and "H" at position 730 of SEQ ID NO: 1.

In one embodiment, the isolated nucleic acid molecule encodes a mutant acetaldehyde-CoA/alcohol dehydrogenase derived from *Clostridium thermocellum*, wherein the mutant protein differs from the wild type protein of SEQ ID NO: 1 by a substitution or deletion of the residue "H" at position 734. In a specific embodiment, the residue "H" has been replaced with "R" or another conserved substitution. In another specific embodiment, "H" at position 734 has been substituted with a non-conserved substitution. In another specific embodiment, "G" at position 553 has been substituted with "R" or another non-conserved substitution. In a further specific embodiment, "D" at position 494 has been substituted with "G" or another non-conserved substitution.

By "conserved substitution" it is meant a substitution of a non-polar (hydrophobic) residue for another non-polar (hydrophobic) residue such as I, V, L or M for one another, a substitution of one polar (hydrophilic), non-charged residue for another polar, non-charged residue such as Q for N, G for S, or vice versa, or a substitution of a charged residue for another similarly charged residue such as K, R or H for one another, or D for E or vice versa. On the other hand, non-conservative substitutions include the substitution of a non-polar (hydrophobic) residue such as I, V, L, A, M for a polar (hydrophilic) residue such as C, Q, D, K and/or vice versa.

In another embodiment, the isolated nucleic acid molecule encodes a mutant acetaldehyde-CoA/alcohol dehydrogenase derived from a species other than *Clostridium thermocellum*, wherein the mutant protein differs from the native protein of that species by a substitution or deletion of the residue "H" at a position corresponding to position 734 of SEQ ID NO: 1, such as a substitution of "H" with "R" or another conserved substitution.

The term "corresponding to" as used in this context refers to the amino acid position of a protein of interest that aligns with position 734 of SEQ ID NO: 1 when such protein of interest and SEQ ID NO: 1 are aligned using an art-acceptable protein alignment program, including the BLAST pairwise alignment, or the well known Lipman-Pearson Protein Alignment program with the following choice of parameters: Ktuple=2, Gap Penalty=4, and Gap Length Penalty=12.

In other embodiments, the isolated nucleic acid molecule encodes a mutant acetaldehyde-CoA/alcohol dehydrogenase, wherein the mutant protein differs from the wild type protein by a substitution or deletion of a residue that is not conserved among species. In a specific embodiment, the mutant protein is derived from *C. thermocellum* and differs from the native protein by a substitution or deletion of the residue "P" at position 704; for example, a substitution of "P" with "L". In another specific embodiment, the mutant protein is derived from *C. thermocellum* and differs from the native protein by a substitution or deletion of the residue "G" at position 553; for example, a substitution of "G" with "R". In a further specific embodiment, the mutant protein is derived from *C. thermocellum* and differs from the native protein by a substitution or deletion of the residue "D" at position 494; for example, a substitution of "D" with "G".

In still other embodiments, the mutant protein contains multiple point mutations. An example is provided herein, the mutant Cthe_0423 protein as set forth in SEQ ID NO: 2, which contains an H to R substitution at position 734 and a P to L substitution at position 704.

In further embodiments, the present invention provides isolated nucleic acid molecules coding for a mutant protein which contains only an ADH domain, without an ALDH domain, in combination with one or more point mutations described above. The ADH domain of such a mutant protein can derive from the Cthe_0423 protein or its two-domain homologs, or from native iron-binding alcohol dehydrogenases containing only an ADH domain without any ALDH domain. Examples of iron-binding alcohol dehydrogenases containing only an ADH domain without an ALDH domain include those from *C. thermocellum* (Cthe_0394, Cthe_2579 and Cthe_0101, having 29%, 28% and 25% to the ADH domain of Cthe_0423), *Z. mobilis* (ZMO1596 and ZMO1771, having 35% and 23% identity with the ADH domain of Cthe_0423), and *Saccharomyces cerevisiae* (about 30% identity with the ADH domain of Cthe_0423).

Mutant proteins created from iron-binding alcohol dehydrogenases (without an ALDH domain) are also referred to as mutant alcohol dehydrogenase. One can align the amino acid sequence of an iron-binding alcohol dehydrogenase with SEQ ID NO: 1 and identify residues for targeted mutagenesis, e.g., residues defining the active site, or conserved residues.

In accordance with the present invention, the isolated nucleic acid molecules encoding a mutant acetaldehyde-CoA/alcohol dehydrogenase or a mutant alcohol dehydrogenase provided herein are capable of conferring enhanced ethanol tolerance to a microorganism.

By "enhanced ethanol tolerance or resistance" it is meant that microorganisms that express the mutant acetaldehyde-CoA/alcohol dehydrogenase demonstrate improved tolerance to ethanol as compared to microorganisms without expression of the mutant protein.

Ethanol tolerance can be determined by the concentration(s) of ethanol which the microorganisms can tolerate and maintain growth. The concentration of ethanol that can be tolerated by a strain can be increased by 15%, 20%, 30%, or 50% or higher, as a result of the expression of a mutant protein. As demonstrated herein below, *C. thermocellum* strains expressing a mutant acetaldehyde-CoA/alcohol dehydrogenase with a desirable genetic modification (e.g., the combination of an H to R substitution at position 734 and a P to L substitution at position 704) are able to grow in the presence of 5% w/v ethanol, whereas *C. thermocellum* strains without such mutant protein cannot. See FIG. 4E.

Alternatively, ethanol tolerance can be determined by the growth profile (the duration of the lag phase, the doubling time, or the maximum density) in the presence of ethanol at a given concentration, and enhanced tolerance can manifest as a shorter lag time (e.g., shortened by 10%, 20%, 30% or 50% or greater), a shorter doubling time (e.g., shortened by 10%, 20%, 30% or 50% or greater) or a higher cell density reached at the end of the exponential growth phase (e.g., 25%, 50%, 75%, 100%, 150%, 200%, 500%, or even 1000% or higher cell density). See FIGS. 4C-4D.

In accordance with the present invention, the isolated nucleic acid molecules encoding a mutant acetaldehyde-CoA/alcohol dehydrogenase or mutant alcohol dehydrogenase can confer an enhanced ethanol tolerance phenotype to a native microorganism (i.e., from which the isolated nucleic acid is obtained), or to a heterologous microorganism. For example, the nucleic acid molecule encoding the mutant Cthe_0423 protein (SEQ ID NO: 2) from *C. thermocellum* can be introduced into other *Clostridium* species, or other bacterial species, or to fungal species, to provide enhanced tolerance to ethanol.

In another aspect, the present invention provides expression vectors that achieve expression of the isolated nucleic acid molecules described above in a microbial host.

Generally, the nucleotide sequence coding for a mutant protein is placed in an operably linkage to a promoter and a 3' termination sequence that are functional in a recipient microbial host. The promoter can be a constitutive promoter or an inducible promoter. The promoter can be the native promoter of the gene being expressed, or a heterologous promoter from a different gene. Heterologous promoters suitable for use in expression in a bacterial host include, for example, the lac promoter, T7, T3 and SP6 phage RNA polymerase promoters, and the adhB promoter. Specific examples of promoters suitable for use in expression in yeast including *S. cerevisiae* include adh1+ (constitutive high expression), fbp1+ (carbon source responsive), a tetracycline-repressible system based on the CaMV promoter, and the nmt1+ (no message in thiamine) promoter. These and other examples of promoters are well documented in the art.

A variety of vector backbones can be used for purpose of the present invention. Choices of vectors suitable for transformation and expression in bacteria and fungi have been well documented in the art. For example, plasmids have been reported for transformation and expression in *Clostridium* species, such as pIKm1 (Tyurin et al., *Applied and Environmental Microbiology*, 70:883-890, 2004); in *Zymomonas*, such as the pZB serial plasmids developed based on *Zymomonas* cryptic plasmid, as described in U.S. Pat. Nos. 5,712,133, 5,726,053, and 5,843,760; and a cloning-compatible broad-host-range destination vector described by Pelletier et al. (*J. Proteome Research* 7(8):3319-3328, 2008), among others.

In addition to the mutant protein expression unit, the expression vector can include other sequences where appropriate, such as sequences for maintenance and selection of the vector, e.g., a selection marker gene and a replication origin. The selection marker gene can be a gene that confers resistance to antibiotics such as ampicillin resistance (Amp$^r$), tetracycline resistance (Tet$^r$), neomycin resistance, hygromycin resistance, and zeocin resistance (Zeo$^r$) genes, or a gene that provides selection based on media supplement and nutrition.

The vector can be a replicative vector (such as a replicating circular plasmid), or an integrative vector that mediates the introduction of the vector into a recipient cell and subsequent integration of the vector into the host genome for chromosomal expression.

For industrial applications, ethanol generated from the biomass pretreatments will select for plasmid maintenance where the mutant protein expression confers an advantage to the strain (i.e., enhanced tolerance to ethanol) in the absence of additional marker or antibiotic selection. Alternatively and preferably, the desired expression unit (such as the mutant protein coding sequence operably linked to a promoter) is integrated into the chromosome of the microorganism for expression and enhanced stability. Methods for chromosomal integration in bacteria include modified homologous Campbell-type recombination (Kalogeraki et al., *Gene* 188(1):69-75, 1997) or transposition (Koch et al., *J Microbiol Meth*, 45(3):187-195, 2001). Methods for chromosomal integration in yeast are well known and are described in Amberg et al. (*Methods in Yeast Genetics*: A Cold Spring Harbor Laboratory Course Manual. New York: Cold Spring Harbor Press; 2005).

An expression vector can be introduced into a microbial host by various approaches, including transformation (e.g., chemical reagent based transformation, or electroporation-based transformation), and conjugation.

In a further aspect, the present invention provides microorganisms that are genetically engineered to express a mutant acetaldehyde-CoA/alcohol dehydrogenase or alcohol dehydrogenase described herein and display enhanced ethanol tolerance. Microorganisms encompassed within the scope of the present invention include both bacteria and fungi.

In some embodiments, the present invention provides bacterial strains having enhanced tolerance to ethanol as a result of expression of a mutant acetaldehyde-CoA/alcohol dehydrogenase or mutant alcohol dehydrogenase described herein. Bacterial strains of interest include both Gram-positive and Gram-negative bacteria. Examples of Gram-positive bacteria include those from the genus of *phylum Firmicutes*, particularly strains of *Acetobacterium, Bacillus, Streptococcus, Clostridium* (e.g., *C. thermocellum*), *Anaerocellum* (e.g., *Anaerocellum thermophilum*), *Caldicellulosiruptor* (e.g., *C. saccharolyticus*), and *Thermoanaerobacter* (e.g., *Thermoanaerobacter* sp. X514). Examples of Gram-negative bacteria of particular interest include those generally considered medically safe, such as *Zymomonas* sp. (e.g., *Z. mobilis*), *E. coli, Gluconobacter* sp. (e.g., *Gluconobacter* oxydans, previously known as *Acetobacter* suboxydans), *Cyanobacteria*, Green sulfur and Green non-sulfur bacteria.

Fungal strains contemplated by the present invention include filamentous and unicellular fungal species, particularly the species from the class of Ascomycota, for example, *Saccharomyces* sp., *Kluyveromyces* sp., *Pichia* sp., *Candida* sp., and *Schizosaccharomycetes* sp. Preferred fungal strains contemplated by the present invention are *S. cerevisiae, S. pombe*, and *Pichia pastoris*.

In one embodiment, a microbial strain having enhanced ethanol tolerance is created by introducing, e.g., via transformation, an exogenous expression vector into the strain which contains the coding sequence of a mutant protein described herein. Alternatively, a microbial strain having enhanced ethanol tolerance can be generated by specifically targeting the gene coding for acetaldehyde-CoA/alcohol dehydrogenase (AdhE gene) or for alcohol dehydrogenase within the strain for mutagenesis and screening for mutants with enhanced ethanol tolerance.

In some embodiments, the nucleic acid molecule on the expression vector that encodes the mutant protein is derived from the endogenous wild type gene from the microorganism receiving the expression vector. In other embodiments, the nucleic acid molecule on the expression vector that encodes the mutant protein is heterologous to the microbial recipient of the expression vector.

The genetically engineered microbial strains of the present invention, which display enhanced tolerance to ethanol as a result of expression of a mutant acetaldehyde-CoA/alcohol dehydrogenase or mutant alcohol dehydrogenase, can be additionally modified as appropriate. For example, Z. mobilis strains can be additionally modified in order to expand the range of substrates that can be utilized by the strains for efficient ethanol production. For instance, Z. mobilis strains can be introduced with additional genes so that the strains can ferment xylose, arabinose or other pentose sugars as the sole carbon source to produce ethanol. See, e.g., U.S. Pat. No. 5,514,583. Additionally, yeast strains, particularly S. cerevisiae strains, can be additionally modified to have an enhanced ability to ferment xylose, arabinose or other pentose sugars to produce ethanol. For example, yeast cells can be modified to overexpress (via transformation with additional expression unit(s)) xylose reductase, xylulokinase, or xylose isomerase; or modified to have reduced expression of xylitol dehydrogenase, PHO13 or a PHO13 ortholog. See, e.g., U.S. Pat. No. 7,285,403, US 20060234364 A1, and US 20080254524 A1, the teachings of which are incorporated herein by reference.

The genetically engineered microbial strains of the present invention are particularly useful for production of biofuels based on fermentation of biomass materials. Therefore, in a further aspect, the present invent provides a method of producing biofuels from cellulosic biomass based on use of the microbial strains of the present invention that are able to grow at elevated concentrations of ethanol.

Biofuels contemplated by the present invention include particular the types of biologically produced fuels, such as bioalcohols, based on the action of microorganisms and enzymes through fermentation of biomass materials. Examples of bioalcohols include ethanol, butanol, and propanol.

In a typical cellulosic biomass to alcohol process, raw cellulosic biomass material is pretreated in order to convert, or partially convert, cellulosic and hemicellulosic components into enzymatically hydrolyzable components (e.g., poly- and oligo-saccharides). The pretreatment process also serves to separate the cellulosic and hemicellulosic components from solid lignin components also present in the raw cellulosic material. The pretreatment process typically involves reacting the raw cellulosic biomass material, often as a finely divided mixture or slurry in water, with an acid, such as sulfuric acid. Other common pretreatment processes include, for example, hot water treatment, wet oxidation, steam explosion, elevated temperature (e.g., boiling), alkali treatment and/or ammonia fiber explosion. The pretreated biomass is then treated by a saccharification step in which poly- and oligo-saccharides are enzymatically hydrolyzed into simple sugars. The free sugars and/or oligosaccharides produced in the saccharification step are then subjected to fermentation conditions for the production of ethanol or butanol, for example. Fermentation can be accomplished by combining one or more fermenting microorganisms with the produced sugars under conditions suitable for fermentation.

One can also add enzyme to the fermentor to aid in the degradation of substrates or to enhance alcohol production. For example, cellulase can be added to degrade cellulose to glucose simultaneously with the fermentation of glucose to ethanol by microorganisms in the same fermentor. Similarly, a hemicellulase can be added to degrade hemicellulose.

It is advantageous to utilize the genetically modified microbial strains described herein that display enhanced resistance to ethanol and are able to continue fermentation despite ethanol present in the fermentation broth.

For purpose of fermentation, one strain or a mixture of several strains, some or all of which display enhanced tolerance to ethanol or other inhibitors, can be used.

Specific fermentation conditions can be determined by those skilled in the art, and may depend on the particular feedstock or substrates, the microorganisms chosen and the type of biofuel desired.

After fermentation, alcohol is separated from the fermentation broth by any of the many conventional techniques known to separate alcohol from aqueous solutions, including evaporation, distillation, solvent extraction and membrane separation. Particles of substrate or microorganisms may be removed before separation to enhance separation efficiency.

The present invention is further illustrated and by no means limited by the following examples.

Example 1

The following examples demonstrate that mutations within a single gene provided a microorganism with enhanced tolerance to ethanol.

An ethanol tolerant C. thermocellum strain (also referred in this example as an ethanol-adapted strain or a mutant strain) was provided as a gift from Prof. Herbert J. Strobel at University of Kentucky, Lexington, Ky. This strain was derived from C. thermocellum strain ATCC 27405 according to an ethanol adaptation procedure described by Williams et al. (2007), supra.

Strain ATCC 27405 typically could not grow when the exogenous ethanol concentration was greater than 1% (w/v), while the ethanol-adapted strain tolerated at least ethanol at 5%. Wild type cells had a faster growth rate and higher cell density as compared to the ethanol adapted strain in the absence of ethanol. However, in the presence of even small amounts of ethanol, the growth rate and cell density of wild type cultures dramatically decreased, while relatively little negative impact was observed for the ethanol-adapted strain in the presence of ethanol of up to 5%. See FIG. 1 of Williams et al. (2007), supra.

FIG. 1 shows net ethanol and acetate production from the wild type ("Cthe_WT") and mutant ("Cthe_EA") strains. Acetate production was similar between strains in the presence or absence of ethanol. The mutant strain still produced ethanol (some alcohol dehydrogenases can oxidize ethanol), and produced more ethanol in the presence of added ethanol. The final biomass of the mutant strain was much lower than the wild type strain. The mutant strain had higher ethanol production per $OD_{600nm}$, but grew more slowly.

Genomes for the wild type and mutant strains were sequenced using both the Roche 454 Genome Sequencer FLX System (454 Life Sciences, Branford, Conn.) and microarray re-sequencing, according to manufacturer's instructions. 454 resequencing identified 500 mutated loci in the ethanol tolerant mutant, and microarray resequencing identified 425 mutated loci in the ethanol tolerant mutant.

The distribution of mutations in the genome was analyzed and found to be non-random. Sixteen (16) hot mutation spots were identified, as shown in Table 1. Seven (7) of the 16 hot spots were found to be related to cellulose degradation. Most hypothetical gene mutations were found to be adjacent to phase/transposase genes.

TABLE 1

Mutational hot spots in ethanol tolerant *C. thermocellum*

| Hot Spot | Products | No of mutations |
|---|---|---|
| 1 | Ig-like, group 2 and cellulose-binding | 5 |
| 2 | redox-sensing tc repressor Rex and bifunctional acetaldehyde-CoA/alcohol dehydrogenase | 4 |
| 3 | hypothetical protein and glycoside hydrolase family protein | 3 |
| 4 | DNA polymerase III PolC and 1-hydroxy-2-methyl-2-(E)-butenyl 4-diphosphate synthase | 3 |
| 5 | Tn7-like transposition protein C and HMG-I and HMG-Y, DNA-binding | 3 |
| 6 | cellulose 1,4-beta-cellobiosidase and leucyl-tRNA synthetase | 5 |
| 7 | cellulosome enzyme, dockerin type I | 6 |
| 8 | phage integrase-like SAM-like and integrase catalytic subunit | 3 |
| 9 | cellulosome enzyme, dockerin type I | 5 |
| 10 | hypothetical protein | 6 |
| 11 | hypothetical protein | 3 |
| 12 | DegT/DnrJ/EryC1/StrS aminotransferase and dTDP-4-dehydrorhamnose 3,5-epimerase | 3 |
| 13 | fibronectin, type III domain | 3 |
| 14 | hypothetical proteins | 11 |
| 15 | hypothetical proteins | 5 |
| 16 | cellulosome anchoring protein, cohesin region | 4 |

Two SNP changes were localized within the Cthe_0423 (adhE) gene, which encodes the bi-functional acetaldehyde-CoA/alcohol dehydrogenase. One of the SNP changes, "C to T", led to a substitution of the original Proline residue with Leucine. The other SNP change, "A to G", led to a substitution of the original Histidine residue with Arginine. Both changes appear in the C-terminal, iron alcohol dehydrogenase domain region of the bifunctional protein. The wild type and the mutant protein sequences are set forth in FIG. 2A (SEQ ID NOS: 1 and 2, respectively), with the two amino acid positions involved in the SNP changes underlined.

Figure 5B:
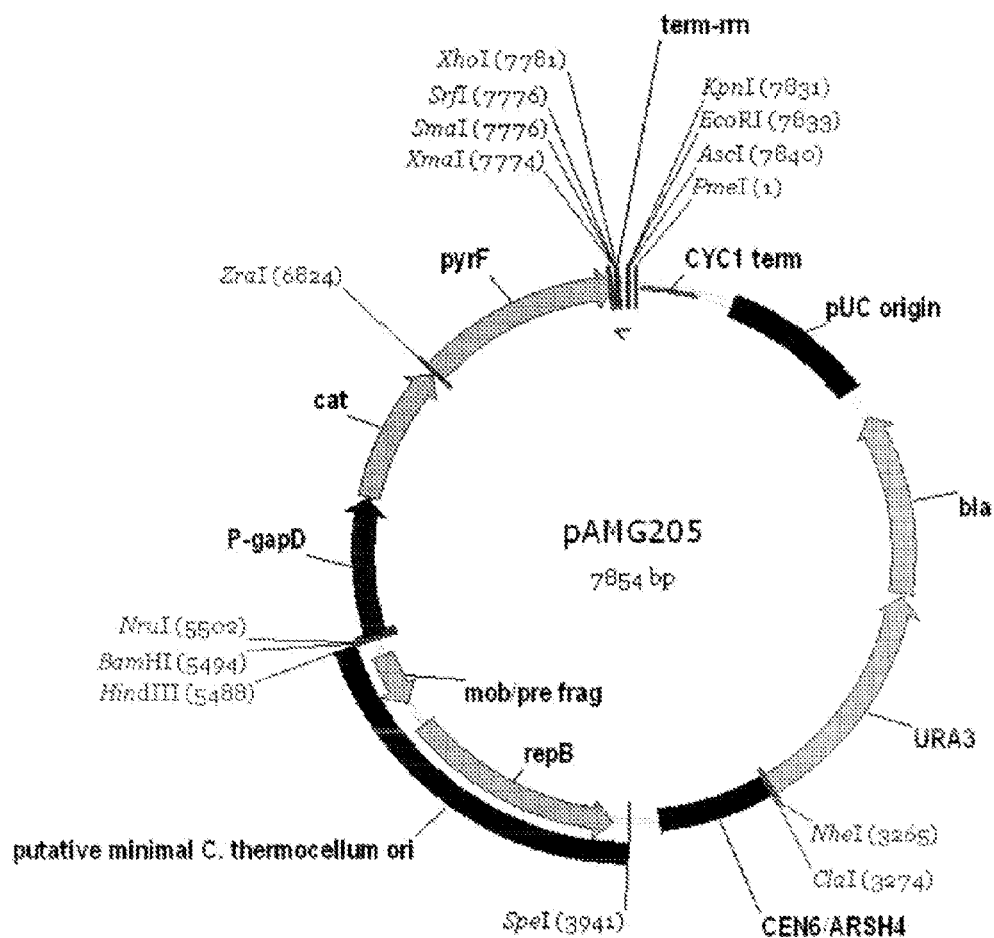

To test the effect of the Cthe_0423 mutant adhE gene encoding the mutant polypeptide of SEQ ID NO: 2 on ethanol tolerance, the wild type and mutant genes were separately inserted into plasmid pAMG205 (see FIGS. 5A-5B for its sequence and map), replacing the pyrF gene and resulting in plasmids pAMG233 and pAMG229, respectively, and were introduced into *C. thermocellum* DSM 1313 wild-type strain (i.e. adhE+) by electroporation. Strains containing plasmid were selected and maintained by culturing in the presence of the antibiotic thiamphenicol under anaerobic conditions. Cells of the *C. thermocellum* DSM 1313 wild-type strain were also transformed with the plasmid pAMG226 (pAMG205DpyrF) for use as control. As shown in FIGS. 4A-4E, only *C. thermocellum* transformed with mutant adhE can grow with 5% (v/v) ethanol added. Ethanol dose effect was clearly observed. Therefore, the mutant copy of the adhE gene conferred the original ethanol tolerance phenotype to a different wild type strain. In addition, wild-type growth rates were achieved in the DSM 1313 strain transformed with the mutant adhE gene in the absence of selection pressure.

Example 2

Mutant Selection and Characterization of Additional Ethanol-Tolerant Strains

Strain and Culture Conditions.

*C. thermocellum* ATCC 27405 was obtained from the American Type Culture Collection (Manassas, Va.). A single colony was isolated and denoted as wild-type (WT). Chemically defined Media for Thermophilic Clostridia (MTC) medium was prepared according to the concentrations listed in Table 2. All chemicals were reagent grade and obtained from Sigma (St. Louis, Mo.), unless indicated otherwise. Solution A contained either Avicel PH105 (FMC Biopolymer, Philadelphia, Pa.) or cellobiose supplemented with appropriate amounts of DI water (Milli-Q). Solution B, C, D, E, and F were injected aseptically into Solution A using a syringe. Prior to combining all the solutions, they were purged with $N_2$ (Airgas Northeast, White River Junction, Vt.) and sterilized by autoclaving at 121° C. for 45 minutes except for Solution A with cellobiose which was autoclaved for 25 minutes.

TABLE 2

Recipe of medium used for the cultivation of *Clostridium thermocellum*

| | Chemicals | Reaction, g/L | Stock, g/L |
|---|---|---|---|
| Solution A | Avicel or cellobiose | 5.0 | |
| Solution B (*25) | Citric acid potassium salt | 2.0 | 50 |
| | Citric acid monohydrate | 1.25 | 31.25 |
| | $Na_2SO_4$ | 1.0 | 25 |
| | $KH_2PO_4$ | 1.0 | 25 |
| | $NaHCO_3$ | 2.5 | 62.5 |
| Solution C (*50) | Urea | 5.0 | 250 |
| | $NH_4Cl$ | 1.5 | 75 |
| Solution D (*50) | $MgCl_2 \cdot 6H_2O$ | 1.0 | 50 |
| | $CaCl_2 \cdot 2H_2O$ | 0.2 | 10 |
| | $FeCl_2 \cdot 4H_2O$ | 0.1 | 5 |
| | L-Cysteine hydrochloride monohydrate | 1.0 | 50 |
| Solution E (*50) (Vitamins) | Pyridoxamine dihydrochloride | 0.02 | 1 |
| | Para-aminobenzoic acid | 0.004 | 0.2 |
| | D-Biotin | 0.002 | 0.1 |
| | Vitamin $B_{12}$ | 0.002 | 0.1 |
| Solution F (*10) | MOPS sodium salt (buffer, for bottle culture) | 10 | 100 |

Adaptation of *C. thermocellum* in Ethanol.

Adaptation of *C. thermocellum* was performed by duplicate serial transfers in crimp-sealed 25 ml Balch tubes. The tubes were sealed empty and purged with $N_2$ and sterilized by autoclaving at 121° C. The tubes were then injected with 9 ml MTC media containing Avicel or cellobiose. Ethanol, also purged with $N_2$, was added to each tube using a 1 ml syringe to have a final concentration of 0 to 50 g/L with an increment of 5 g/L. Each inoculation/transfer was 10% volume (1 ml). Cultures were grown in an incubator (New Brunswick Scientific, Innova 4080) with temperature controlled at 55° C. and rotation speed set at 200 rpm.

Serial transfer to obtain ethanol tolerant mutants involved inoculation into medium with elevated ethanol concentrations alternated with medium without added ethanol. The parameter R was defined as the ratio of final OD over initial OD for cellobiose and the ratio of final pellet nitrogen over initial pellet nitrogen for Avicel within 72 hours incubation. The criteria for transfer were (a) transfer to higher ethanol concentration if R>=4, (b) maintain current ethanol concentration if 2<=R<4, and (c) transfer to previous ethanol concentration if R<2. Single colonies of ethanol tolerant strains were isolated from the final cultures and denoted as E50A for adaptation using Avicel and E50C for adaptation using cellobiose.

Adaptation.

Figure 6:
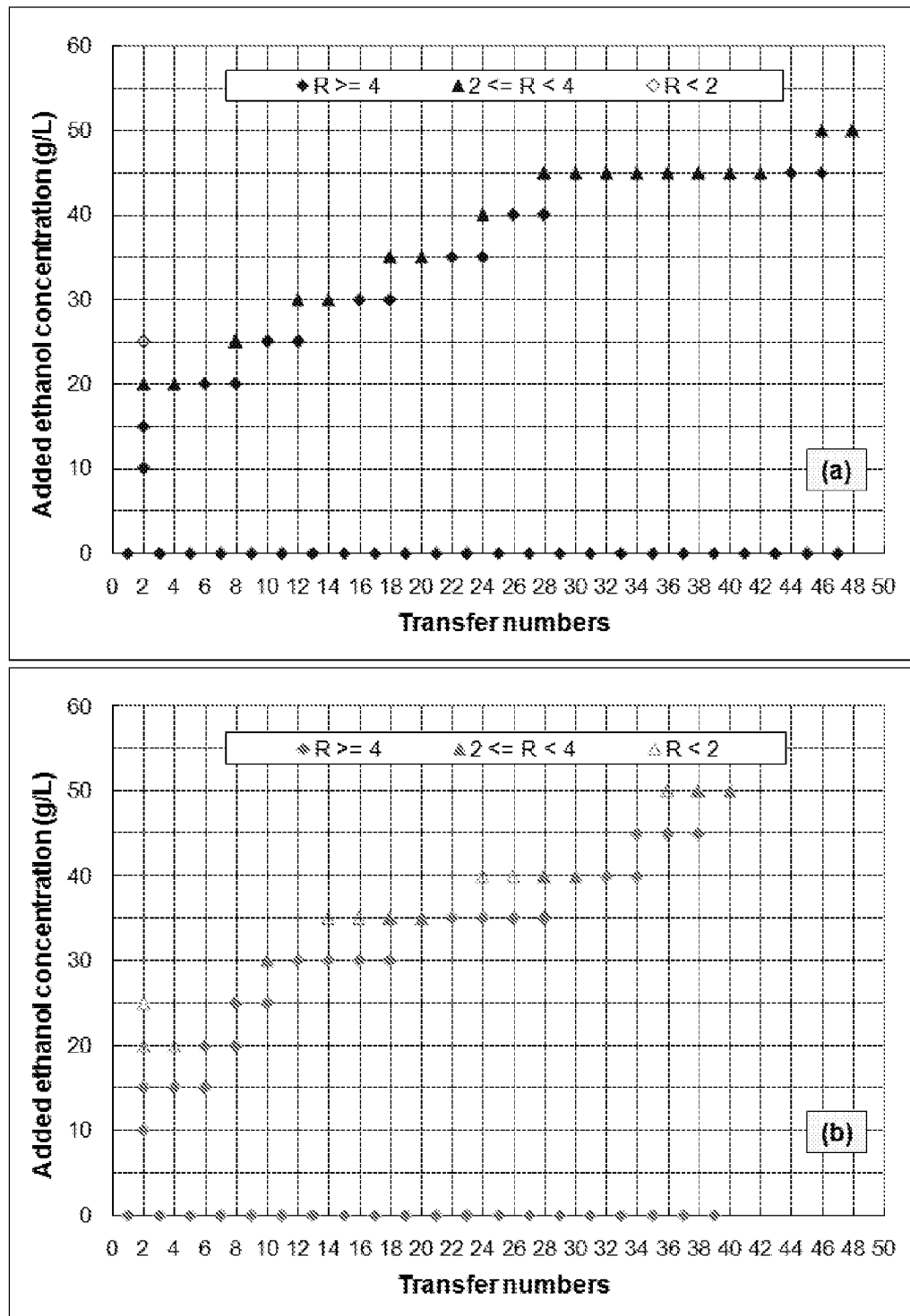
FIG. 6. Adaptation map for higher ethanol tolerance (a) on Avicel, R is the ratio of final pellet nitrogen over initial pellet nitrogen within 72 hours, (b) on cellobiose, R is the ratio of final OD over initial OD with 72 hours.

A culture of *C. thermocellum* originating from a single colony isolate was sequentially transferred in growth medium containing progressively increasing ethanol concentrations, with every other culture grown in the absence of ethanol, using either crystalline cellulose (Avicel) or cellobiose as the substrate (FIG. 6). The wild-type strain has an ethanol tolerance of ~15 g/L. To attain tolerance to 50 g/L ethanol, adaptation using cellobiose took 40 transfers while adaptation using Avicel took 48 transfers. However, to reach 45 g/L ethanol, it took only 30 transfers for adaptation using Avicel as compared to 36 transfers for adaptation using cellobiose. For these adapted cultures, single pure cultures were isolated for further characterization: E50C isolated from cellobiose-grown cultures, and E50A isolated from Avicel-grown cultures.

Isolation of Single Colonies.

Agar (Fisher Scientific, Pittsburgh, Pa.) solution (18.75 g/L) was prepared and 40 ml was distributed into each of eight 125 ml serum bottles (Wheaton, Millville, N.J.). The bottles were crimp-sealed, purged with $N_2$, and sterilized by autoclaving at 121° C. for 25 minutes. The sterilized bottles were stored in a 60° C. oven to prevent solidification of agar. Sterile anaerobic solutions B, C, D, and E of MTC media, pre-heated to 60° C., were injected into the bottles as per the medium recipe (Table 2). A mixture consisting of yeast extract, cellobiose, and MOPS was purged with $N_2$, filter-sterilized, and injected into the agar-containing bottles, giving a final concentrations of 5 g/L yeast extract, 2 g/L cellobiose, and 10 g/L MOPS. The agar-containing bottles were then transferred into an anaerobic chamber (Coy Laboratory Products, Grass Lake, Mich.). Final adaptation culture (0.5 ml) was inoculated into the first agar-containing bottle followed by serial transfers into the other bottles as follows: 0.5, 0.5, 5, 5, 5, 5, 5 ml. The contents of each of the last five bottles were poured into two Petri dishes (BD Biosciences, Bedford, Mass.). The dishes were allowed to sit for 30 minutes to solidify the agar and then incubated at 55° C. Colonies were picked using a needle after 32 to 48 hours incubation. A picked colony was transferred into a microcentrifuge tube with 1 ml sterilized DI water, which was mixed and injected into a crimp-sealed 125 ml serum bottle with 50 ml Avicel or cellobiose MTC media. The bottle was incubated at 55° C. and 200 rpm. After about 24 hours, stock culture was prepared with 33% glycerol and stored at −80° C.

Characterization of the Ethanol Tolerant Strains.

To determine growth rate without added ethanol, *C. thermocellum* strains WT, E50A, and E50C were cultured in MTC media with Avicel or cellobiose. Crimp-sealed 125 ml serum vials with 35 ml DI water and 0.25 g Avicel or cellobiose were purged with $N_2$ and sterilized by autoclaving at 121° C. After autoclaving, sterile and anaerobic solution B, C, D, E, and F were injected. The vials were then incubated at 55° C. and followed by inoculation of 10% by volume with the inoculum prepared in MTC media with 5 g/L Avicel or cellobiose from stock culture. After inoculation, the bottles were incubated at 55° C. and 200 rpm. Samples were taken at various times for analysis of pellet nitrogen and product concentrations.

To characterize ethanol tolerance of the two adapted strains of *C. thermocellum*, E50A and E50C were cultured in Avicel or cellobiose MTC media with various ethanol concentrations. The preparation of media and inoculum was the same as the above except that ethanol, purged with $N_2$ and supplemented with 2% volume solution D, were injected into each bottle five hours after the inoculation. Samples were taken using syringe at various time points after inoculation.

Analytical Methods.

The optical density (OD) of cultures grown in 25 ml Balch tubes (Bellco Glass, Vineland, N.J.) was measured directly (without sampling) using a Thermo Spectronic Gevesys 10VIS spectrophotometer (Rochester, N.Y.) at 600 nm. Pellet nitrogen, used as a proxy for cell growth for insoluble substrate, was measured using a Shimadzu TOC/TON analyzer equipped with an automatic sampler. Pellet samples were collected by centrifugation of 1 ml sample at 21130 g for five minutes, followed by three washes that involved resuspension of the pellet in 1 ml deionized water, centrifugation as above, and removal of the supernatant. The washed pellet samples were either analyzed directly or stored at −20° C. until analysis. Fermentation product concentrations were obtained using a Waters HPLC system with an Aminex HPX-87H column operated at 60° C.

Effect Of Adaptation.

Figure 7:
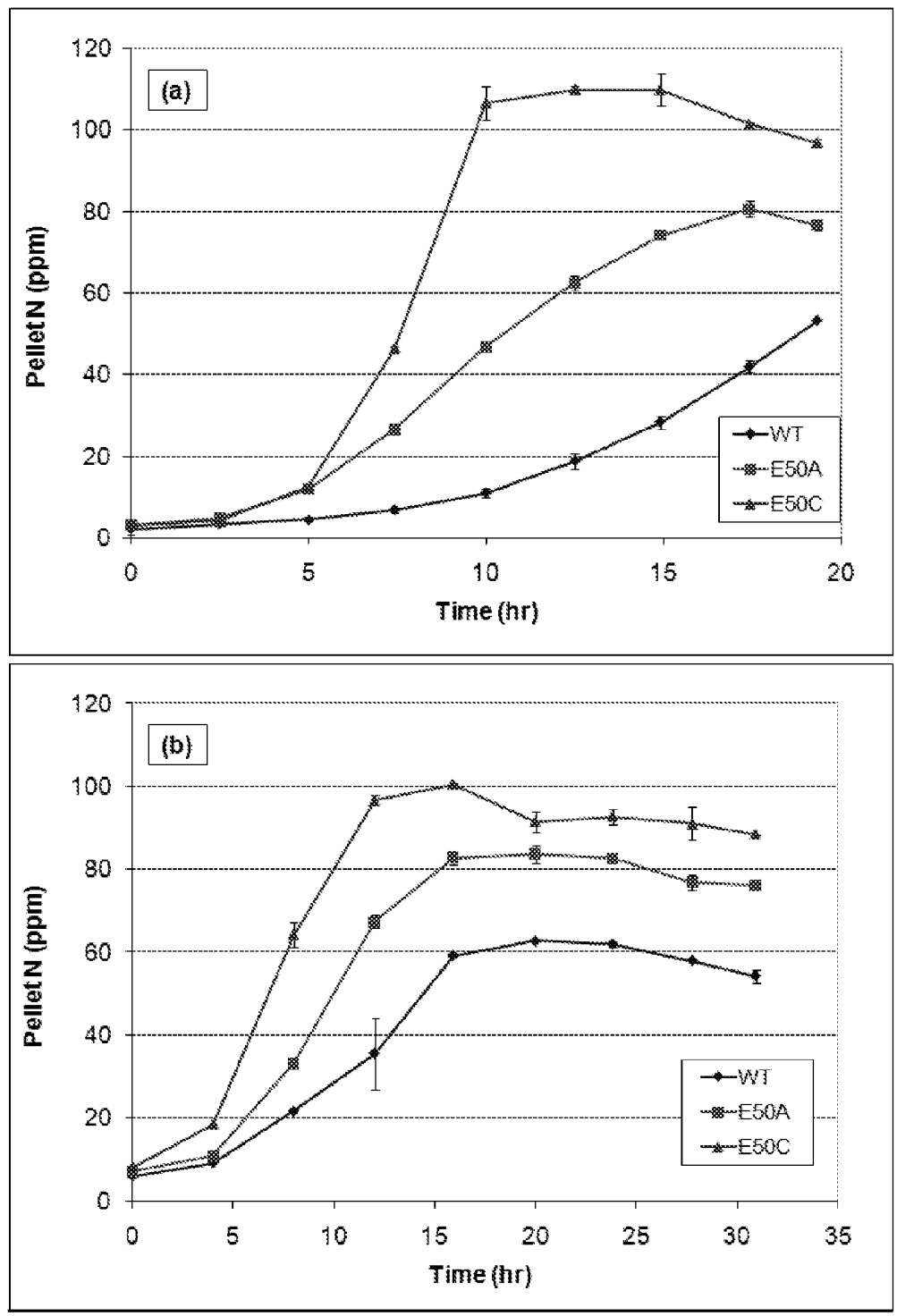
FIG. 7. Comparison of growth (pellet nitrogen curve) among E50A, E50C, and wild type (WT) (a) using cellobiose (b) using Avicel.

Strain E50C, although adapted to tolerate high ethanol concentrations exclusively with cellobiose as the growth substrate, retained its capability to solubilize and grow on crystalline cellulose. A comparison of growth for the wild-type and selected strains using either Avicel or cellobiose is given in FIG. 7. Both E50A and E50C strains grow faster and to a higher cell yield (as measured by total nitrogen content in the cell pellet) than the wild-type strain when no ethanol is added. Among the three strains, strain E50C has the fastest growth rate using either cellobiose or Avicel, while the wild-type strain has the slowest growth rate (Table 3).

TABLE 3

Specific growth rates for E50A, E50C, and wild-type strains using cellobiose or Avicel as substrate.

| | Specific growth rate, $hr^{-1}$ | |
|---|---|---|
| | Cellobiose | Avicel* |
| Wild-type | 0.141 ± 0.017 | 0.158 ± 0.053 |
| E50A | 0.224 ± 0.004* | 0.228 ± 0.090 |
| E50C | 0.334 ± 0.010 | 0.280 ± 0.031 |

*Used only early exponential phase data.

Figure 8:
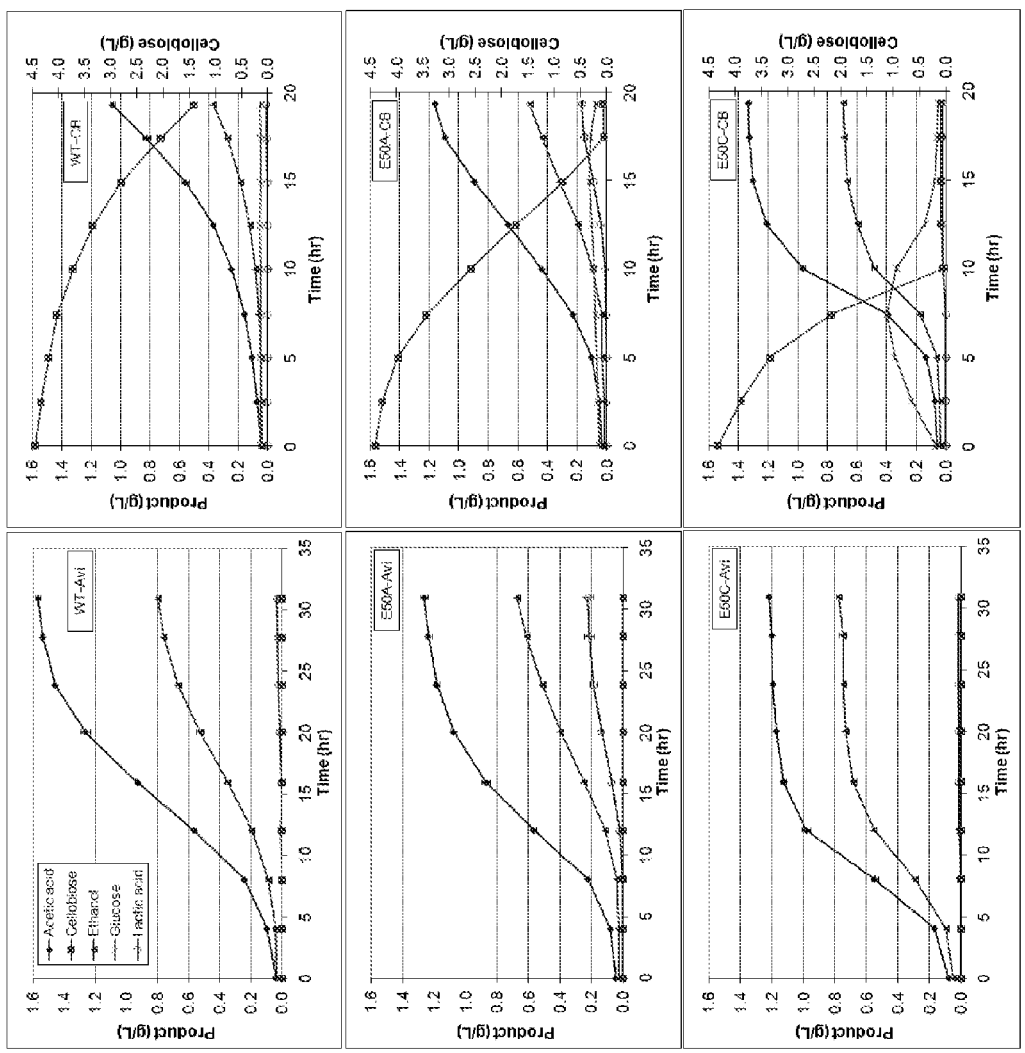
FIG. 8. Comparison of products among wild type (WT), E50A, and E50C using cellobiose (CB) and Avicel.

Product profiles for the three strains during the course of growth on cellobiose and Avicel are shown in FIG. 8. Acetic acid is the major product for all three strains on both substrates, followed by ethanol and lactic acid, with E50A producing much more lactic acid than either E50C or WT. Cellobiose was consumed in 10 hours for E50C and in 17.5 hours for E50A, while there was still about 1.5 g/L cellobiose left after 20 hours for the WT strain (FIG. 8). Among the three strains, E50C has the lowest mass ratio of organic acids (acetate plus lactate) to ethanol (Table 4). During growth on cellobiose, significant glucose accumulation is observed for E50C and to a less extent for E50A, but glucose is consumed when cellobiose is exhausted in both cultures. During growth on Avicel, although substrate consumption was not readily followable, E50C completed product formation most quickly among the three strains and also had the lowest ratio of organic acids to ethanol in the fermentation broth. The wild type had a final product titer of about 2.4 g/L compared to 2.1 and 2.0 g/L for E50A and E50C respectively.

TABLE 4

Mass ratio of organic acids (acetate plus lactate) to ethanol for wild type, E50A, and E50C on cellobiose or Avicel.

|  | Wild type | E50A | E50C |
| --- | --- | --- | --- |
| Cellobiose | | | |
| Acetic acid (a) | 1.08 | 1.16 | 1.33 |
| Ethanol (e) | 0.37 | 0.52 | 0.68 |
| Lactic acid (l) | 0.00 | 0.18 | 0.00 |
| (a + l)/e | 2.92 | 2.58 | 1.96 |
| a/e | 2.92 | 2.23 | 1.96 |
| Avicel | | | |
| Acetic acid (a) | 1.58 | 1.25 | 1.22 |
| Ethanol (e) | 0.79 | 0.66 | 0.78 |
| Lactic acid (l) | 0.00 | 0.21 | 0.00 |
| (a + l)/e | 2.00 | 2.21 | 1.56 |
| a/e | 2.00 | 1.89 | 1.56 |

Effect of Ethanol on Growth.

Figure 9:
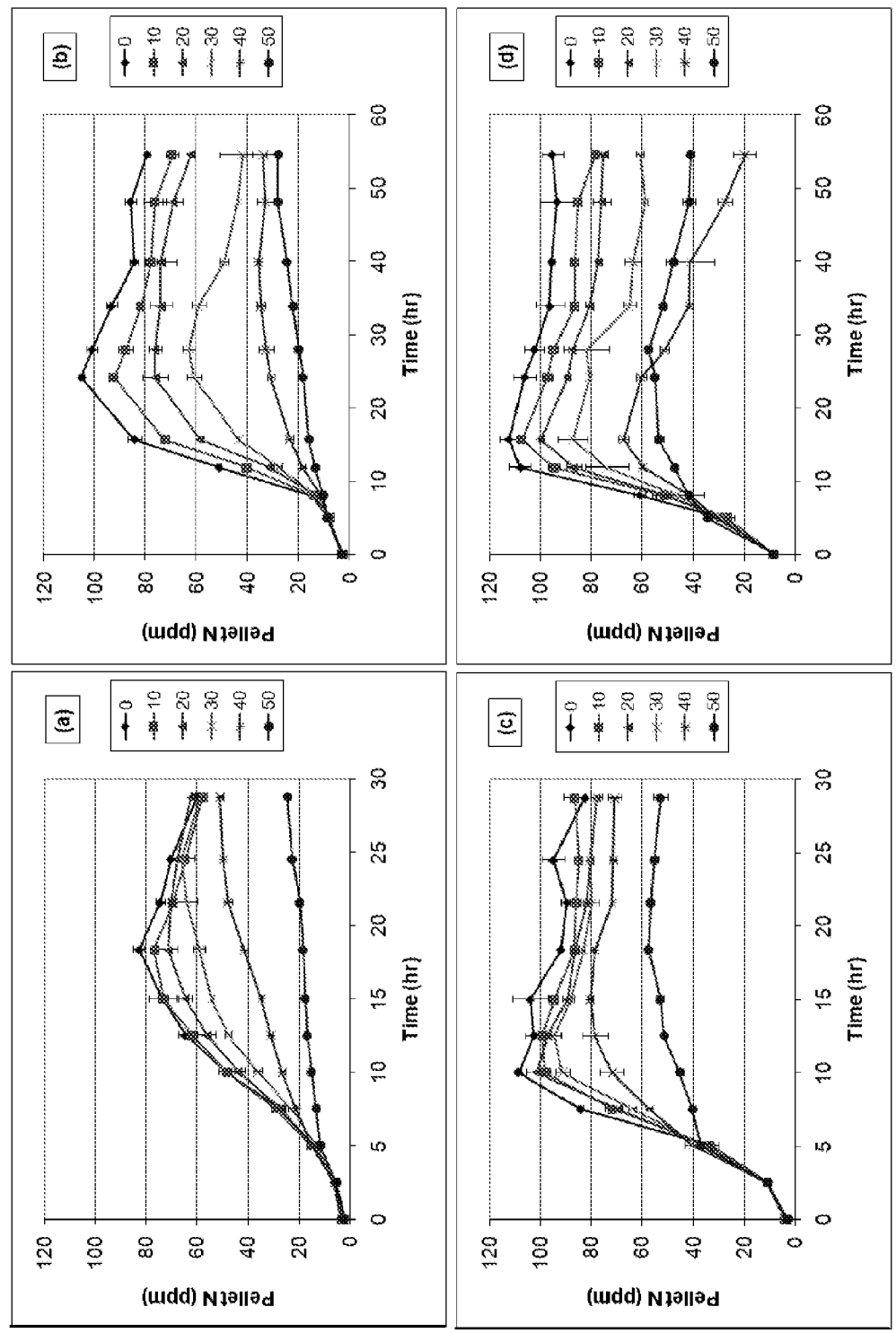
FIG. 9. Growth of selected strains in various ethanol concentrations (0-50 g/L) (a) E50A on cellobiose (b) E50A on Avicel (c) E50C on cellobiose (d) E50C on Avicel. Ethanol, purged with $N_2$ and supplemented with 2% volume solution D, were injected five hours after the inoculation.

The ethanol tolerant strains were evaluated for growth characteristics in response to various ethanol concentrations up to 50 g/L (FIG. 9). Similar to growth patterns observed in the absence of ethanol (FIG. 7), E50C grew more rapidly on both cellobiose and Avicel, as compared to E50A, under all conditions tested. Ethanol concentrations higher than 30 g/L caused significant growth inhibition for both tolerant strains, which was more pronounced during growth on Avicel. This indicates that both strains reached a critical sensitivity threshold around 30-40 g/L ethanol, which was more clearly seen when maximum cell concentration (as measured by total nitrogen content in the cell pellet) and growth rate data were examined (FIG. 9). For both E50A and E50C, during growth on either Avicel or cellobiose, the maximum cell concentration decreased with increasing ethanol concentration, with the largest change occurring between 30 and 40 g/L added ethanol.

Genome Sequencing and Analysis.

Genomic DNA for E50A and E50C was extracted using Genomic-tip 500/G (Qiagen, Valencia, Calif.). The DNA samples were shipped on dry ice to the DOE Joint Genome Institute (JGI, Walnut Creek, Calif.), and samples were sequenced using JGI's whole-genome shotgun sequencing method to produce a high-quality draft sequence. Sequencing was initiated with creation of 3-Kb, 8-Kb, and 40-Kb DNA libraries, performed from both sides of the library insert, producing paired ends typically resulting in approximately 8-9× depth. Sequenced reads were aligned using MAQ (Li, H. et al., 2008. Mapping short DNA sequencing reads and calling variants using mapping quality scores. Genome Res. 18:1851-1858). A report with Single Nucleotide Polymorphisms (SNPs) and statistical analysis was returned. The genes were annotated according to the C. thermocellum ATCC 27405 analysis file on the website of Oak Ridge National Laboratory.

Genetic Changes in the Ethanol Tolerant Strains.

In an effort to unravel the genetic changes associated with the ethanol tolerance phenotype in C. thermocellum, the genomes of the mutant strains were sequenced to identify Single Nucleotide Polymorphisms (or SNPs) or other alterations in their genomic sequences. Genome sequencing revealed 10 and 39 nonsynonymous SNPs in the E50A and the E50C strain, respectively. In addition, there were 6 synonymous SNPs in E50C; non-coding regions in E50A and E50C strains contained 5 and 7 SNPs, respectively. Six mutated genes were shared by both strains including four with identical genetic changes. Specifically genes Cthe0390 (putative glucokinase), Cthe1866 (argD, acetylornithine aminotransferase), Cthe2699 (putative transcriptional regulator), and Cthe2870 (protein of unknown function) had identical changes in both strains.

Cthe0423 (adhE, bi-functional aldehyde/alcohol dehydrogenase, involved in ethanol production from acetyl-CoA) and Cthe0953 (pyrB, aspartate carbamoyltransferase, involved in pyrimidine biosynthesis from carbamoyl phosphate), on the other hand, were independently mutated in these two strains. Since these independent mutations suggest a functional role in ethanol tolerance, homology based structural modeling [using I-TASSER (23)] was used to identify the location of altered amino acid residues within the protein structures to gain insight into the effect of the mutations. The two independent mutations in the AdhE protein in strains E50A ("G" at position 553 to "R"; SEQ ID NO:5; FIG. 10) and E50C ("D" at position 494 to "G"; SEQ ID NO:6; FIG. 10) both lay within the nicotinamide co-factor binding site of the ADH domain in the proteins with potential direct implications in enzymatic catalysis.

What is claimed is:

1. An isolated nucleic acid molecule, which confers enhanced ethanol tolerance to a microorganism and encodes a protein comprising a mutant alcohol dehydrogenase (ADH) domain of an acetaldehyde-CoA/alcohol dehydrogenase or alcohol dehydrogenase, said mutant ADH domain comprising an amino acid alteration at one or more residues corresponding to positions 494, 552, 553, 554, 557, 560, 604, 605, 607, 626, 627, 647, 653, 660, 664, 704, 730, 734, or 744 of SEQ ID NO:1.

2. The isolated nucleic acid molecule of claim 1, wherein said acetaldehyde-CoA/alcohol dehydrogenase or said alcohol dehydrogenase is of a bacterial or fungal origin.

3. The isolated nucleic acid molecule of claim 2, wherein said bacterial origin is *Clostridium*.

4. The isolated nucleic acid molecule of claim 3, wherein said *Clostridium* is *C. thermocellum*.

5. The isolated nucleic acid molecule of claim 1, wherein said mutant ADH domain shows altered co-factor specificity.

6. The isolated nucleic acid molecule of claim 5, wherein said altered co-factor specificity is preferential use of NADPH over NADH.

7. The isolated nucleic acid molecule of claim 1, wherein said amino acid residue is H at a position corresponding to position 730 or 734 of SEQ ID NO: 1.

8. The isolated nucleic acid molecule of claim 7, wherein said mutant ADH domain comprises the substitution of H with R at a position corresponding to position 734 of SEQ ID NO: 1.

9. The isolated nucleic acid molecule of claim 1, wherein said mutant ADH domain comprises a substitution of P with L at a position corresponding to position 704 of SEQ ID NO: 1.

10. The isolated nucleic acid molecule of claim 1, wherein said mutant ADH domain comprises a substitution of G with R at a position corresponding to position 553 of SEQ ID NO: 1.

11. The isolated nucleic acid molecule of claim 1, wherein said mutant ADH domain comprises a substitution of D with G at a position corresponding to position 494 of SEQ ID NO: 1.

12. The isolated nucleic acid molecule of claim 1, wherein said mutant ADH domain comprises amino acids 463-864 of SEQ ID NO: 2.

13. The isolated nucleic acid molecule of claim 1, wherein said protein further comprises an acetaldehyde dehydrogenase (ALDH) domain of said acetaldehyde-CoA/alcohol dehydrogenase.

14. The isolated nucleic acid molecule of claim 13, wherein said protein comprises the amino acid sequence of SEQ ID NO: 2.

15. An expression vector comprising the isolated nucleic acid of claim 1.

16. A genetically engineered microorganism with enhanced ethanol tolerance, said microorganism being transformed with the expression vector of claim 15.

17. The microorganism of claim 16, selected from bacteria or fungi.

18. The microorganism of claim 17, wherein said microorganism is a bacterial species selected from *Acetobacterium, Bacillus, Streptococcus, Clostridium, Zymomonas* sp., and *Gluconobacter* sp.

19. The microorganism of claim 17, wherein said microorganism is a fungal species selected from *Saccharomyces* sp., *Kluyveromyces* sp., *Pichia* sp., *Candida* sp., and *Schizosaccharomycetes* sp.

20. The microorganism of claim 16, wherein said acetaldehyde-CoA/alcohol dehydrogenase is native to said microorganism.

21. The microorganism of claim 16, wherein said acetaldehyde-CoA/alcohol dehydrogenase is heterologous to said microorganism.

22. The microorganism of claim 16, wherein said acetaldehyde-CoA/alcohol dehydrogenase comprises the amino acid sequence as set forth in SEQ ID NO: 1.

23. The microorganism of claim 16, wherein said mutant ADH domain comprises amino acids 463-864 of SEQ ID NO: 2.

24. The microorganism of claim 16, wherein said protein comprises the amino acid sequence of SEQ ID NO: 2.

25. The microorganism of claim 16, wherein said nucleic acid molecule comprises the sequence of SEQ ID NO: 5.

26. The microorganism of claim 16, wherein said protein comprises the amino acid sequence of SEQ ID NO: 6.

27. A method of producing alcohol from a cellulosic biomass material, comprising adding a genetically modified microorganism according to any one of claims 16-26 to a fermentation mixture comprising a cellulosic biomass material and/or fermentation substrates derived from said cellulosic biomass material, allowing said microorganism to ferment and produce alcohol, and recover alcohol produced.

* * * * *

UNITED STATES PATENT AND TRADEMARK OFFICE
CERTIFICATE OF CORRECTION

| | | |
|---|---|---|
| PATENT NO. | : 8,629,255 B2 | Page 1 of 1 |
| APPLICATION NO. | : 13/112641 | |
| DATED | : January 14, 2014 | |
| INVENTOR(S) | : Steven Brown et al. | |

It is certified that error appears in the above-identified patent and that said Letters Patent is hereby corrected as shown below:

On the Title Page

Item (73) Assignee should read:

-- (73)   Assignee:   UT-BATTELLE, LLC, Oak Ridge, TN (US)
                            THE TRUSTEES OF DARTMOUTH COLLEGE, Hanover, NH (US) --.

Signed and Sealed this
Tenth Day of June, 2014

Michelle K. Lee
*Deputy Director of the United States Patent and Trademark Office*

SEQUENCE LISTING

<160> NUMBER OF SEQ ID NOS: 9

<210> SEQ ID NO 1
<211> LENGTH: 873
<212> TYPE: PRT
<213> ORGANISM: Clostridium thermocellum

<400> SEQUENCE: 1

Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

```
Thr Tyr Thr Gln Glu Gln Val Asp Lys Ile Phe Phe Glu Ala Ala Met
         35                  40                  45
Ala Ala Asn Lys Met Arg Ile Pro Leu Ala Lys Met Ala Val Glu Glu
         50                  55                  60
Thr Gly Met Gly Val Val Glu Asp Lys Val Ile Lys Asn His Tyr Ala
 65                  70                  75                  80
Ser Glu Tyr Ile Tyr Asn Ala Tyr Lys Asn Thr Lys Thr Cys Gly Val
                     85                  90                  95
Ile Glu Glu Asp Pro Ala Phe Gly Ile Lys Lys Ile Ala Glu Pro Leu
                100                 105                 110
Gly Val Ile Ala Ala Val Ile Pro Thr Thr Asn Pro Thr Ser Thr Ala
            115                 120                 125
Ile Phe Lys Thr Leu Ile Ala Leu Lys Thr Arg Asn Ala Ile Ile Ile
        130                 135                 140
Ser Pro His Pro Arg Ala Lys Asn Ser Thr Ile Glu Ala Ala Lys Ile
145                 150                 155                 160
Val Leu Glu Ala Ala Val Lys Ala Gly Ala Pro Glu Gly Ile Ile Gly
                165                 170                 175
Trp Ile Asp Val Pro Ser Leu Glu Leu Thr Asn Leu Val Met Arg Glu
        180                 185                 190
Ala Asp Val Ile Leu Ala Thr Gly Gly Pro Gly Leu Val Lys Ala Ala
        195                 200                 205
Tyr Ser Ser Gly Lys Pro Ala Ile Gly Val Gly Ala Gly Asn Thr Pro
    210                 215                 220
Ala Ile Ile Asp Asp Ser Ala Asp Ile Val Leu Ala Val Asn Ser Ile
225                 230                 235                 240
Ile His Ser Lys Thr Phe Asp Asn Gly Met Ile Cys Ala Ser Glu Gln
                245                 250                 255
Ser Val Ile Val Leu Asp Gly Val Tyr Lys Glu Val Lys Lys Glu Phe
                260                 265                 270
Glu Lys Arg Gly Cys Tyr Phe Leu Asn Glu Asp Glu Thr Glu Lys Val
        275                 280                 285
Arg Lys Thr Ile Ile Asn Gly Ala Leu Asn Ala Lys Ile Val Gly
        290                 295                 300
Gln Lys Ala His Thr Ile Ala Asn Leu Ala Gly Phe Glu Val Pro Glu
305                 310                 315                 320
Thr Thr Lys Ile Leu Ile Gly Glu Val Thr Ser Val Asp Ile Ser Glu
                325                 330                 335
Glu Phe Ala His Glu Lys Leu Cys Pro Val Leu Ala Met Tyr Arg Ala
                340                 345                 350
Lys Asp Phe Asp Asp Ala Leu Asp Lys Ala Glu Arg Leu Val Ala Asp
        355                 360                 365
Gly Gly Phe Gly His Thr Ser Ser Leu Tyr Ile Asp Thr Val Thr Gln
    370                 375                 380
Lys Glu Lys Leu Gln Lys Phe Ser Glu Arg Met Lys Thr Cys Arg Ile
385                 390                 395                 400
Leu Val Asn Thr Pro Ser Ser Gln Gly Gly Ile Gly Asp Leu Tyr Asn
                405                 410                 415
Phe Lys Leu Ala Pro Ser Leu Thr Leu Gly Cys Gly Ser Trp Gly Gly
                420                 425                 430
Asn Ser Val Ser Asp Asn Val Gly Val Lys His Leu Leu Asn Ile Lys
        435                 440                 445
Thr Val Ala Glu Arg Arg Glu Asn Met Leu Trp Phe Arg Thr Pro Glu
450                 455                 460
```

```
Lys Ile Tyr Ile Lys Arg Gly Cys Leu Pro Val Ala Leu Asp Glu Leu
465                 470                 475                 480

Lys Asn Val Met Gly Lys Lys Ala Phe Ile Val Thr Asp Asn Phe
            485                 490                 495

Leu Tyr Asn Asn Gly Tyr Thr Lys Pro Ile Thr Asp Lys Leu Asp Glu
            500                 505                 510

Met Gly Ile Val His Lys Thr Phe Phe Asp Val Ser Pro Asp Pro Ser
            515                 520                 525

Leu Ala Ser Ala Lys Ala Gly Ala Ala Glu Met Leu Ala Phe Gln Pro
530                 535                 540

Asp Thr Ile Ile Ala Val Gly Gly Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
            580                 585                 590

Met Gly Gln Lys Ala Tyr Phe Ile Ala Ile Pro Thr Ser Ala Gly Thr
            595                 600                 605

Gly Ser Glu Val Thr Pro Phe Ala Val Ile Thr Asp Glu Lys Thr Gly
            610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
                645                 650                 655

Ser Gly Ile Asp Ala Leu Thr His Ala Leu Glu Ala Tyr Val Ser Met
            660                 665                 670

Leu Ala Thr Asp Tyr Thr Asp Ser Leu Ala Leu Arg Ala Ile Lys Met
            675                 680                 685

Ile Phe Glu Tyr Leu Pro Arg Ala Tyr Glu Asn Gly Ala Ser Asp Pro
690                 695                 700

Val Ala Arg Glu Lys Met Ala Asn Ala Thr Ile Ala Gly Met Ala
705                 710                 715                 720

Phe Ala Asn Ala Phe Leu Gly Val Cys His Ser Met Ala His Lys Leu
                725                 730                 735

Gly Ala Phe Tyr His Leu Pro His Gly Val Ala Asn Ala Leu Met Ile
            740                 745                 750

Asn Glu Val Ile Arg Phe Asn Ser Ser Glu Ala Pro Thr Lys Met Gly
            755                 760                 765

Thr Phe Pro Gln Tyr Asp His Pro Arg Thr Leu Glu Arg Tyr Ala Glu
770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
            805                 810                 815

Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
            835                 840                 845

Thr Asn Pro Arg Tyr Pro Leu Met Asn Glu Ile Arg Gln Met Tyr Leu
            850                 855                 860

Asn Ala Tyr Tyr Gly Gly Ala Lys Lys
865                 870
```

<210> SEQ ID NO 2
<211> LENGTH: 873
<212> TYPE: PRT
<213> ORGANISM: Clostridium thermocellum

<400> SEQUENCE: 2

```
Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

Thr Tyr Thr Gln Glu Gln Val Asp Lys Ile Phe Phe Glu Ala Ala Met
        35                  40                  45

Ala Ala Asn Lys Met Arg Ile Pro Leu Ala Lys Met Ala Val Glu Glu
    50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile
    130                 135                 140

Ser Pro His Pro Arg Ala Lys Asn Ser Thr Ile Glu Ala Ala Lys Ile
145                 150                 155                 160

Val Leu Glu Ala Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190

Ala Asp Val Ile Leu Ala Thr Gly Gly Pro Gly Leu Val Lys Ala Ala
        195                 200                 205

Tyr Ser Ser Gly Lys Pro Ala Ile Gly Val Gly Ala Gly Asn Thr Pro
    210                 215                 220

Ala Ile Ile Asp Asp Ser Ala Asp Ile Val Leu Ala Val Asn Ser Ile
225                 230                 235                 240

Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
            260                 265                 270

Glu Lys Arg Gly Cys Tyr Phe Leu Asn Glu Asp Glu Thr Glu Lys Val
        275                 280                 285

Arg Lys Thr Ile Ile Asn Gly Ala Leu Asn Ala Lys Ile Val Gly
    290                 295                 300

Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
            340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
    370                 375                 380

Lys Glu Lys Leu Gln Lys Phe Ser Glu Arg Met Lys Thr Cys Arg Ile
```

-continued

```
            385                 390                 395                 400
        Leu Val Asn Thr Pro Ser Ser Gln Gly Gly Ile Gly Asp Leu Tyr Asn
                            405                 410                 415

Phe Lys Leu Ala Pro Ser Leu Thr Leu Gly Cys Gly Ser Trp Gly Gly
                            420                 425                 430

Asn Ser Val Ser Asp Asn Val Gly Val Lys His Leu Leu Asn Ile Lys
                            435                 440                 445

Thr Val Ala Glu Arg Arg Glu Asn Met Leu Trp Phe Arg Thr Pro Glu
                    450                 455                 460

Lys Ile Tyr Ile Lys Arg Gly Cys Leu Pro Val Ala Leu Asp Glu Leu
        465                 470                 475                 480

Lys Asn Val Met Gly Lys Lys Ala Phe Ile Val Thr Asp Asn Phe
                            485                 490                 495

Leu Tyr Asn Asn Gly Tyr Thr Lys Pro Ile Thr Asp Lys Leu Asp Glu
                        500                 505                 510

Met Gly Ile Val His Lys Thr Phe Phe Asp Val Ser Pro Asp Pro Ser
                    515                 520                 525

Leu Ala Ser Ala Lys Ala Gly Ala Ala Glu Met Leu Ala Phe Gln Pro
                    530                 535                 540

Asp Thr Ile Ile Ala Val Gly Gly Gly Ser Ala Met Asp Ala Ala Lys
        545                 550                 555                 560

Ile Met Trp Val Met Tyr Glu His Pro Glu Val Asp Phe Met Asp Met
                            565                 570                 575

Ala Met Arg Phe Met Asp Ile Arg Lys Arg Val Tyr Thr Phe Pro Lys
                        580                 585                 590

Met Gly Gln Lys Ala Tyr Phe Ile Ala Ile Pro Thr Ser Ala Gly Thr
                    595                 600                 605

Gly Ser Glu Val Thr Pro Phe Ala Val Ile Thr Asp Glu Lys Thr Gly
                610                 615                 620

Ile Lys Tyr Pro Leu Ala Asp Tyr Glu Leu Leu Pro Asp Met Ala Ile
        625                 630                 635                 640

Val Asp Ala Asp Met Met Met Asn Ala Pro Lys Gly Leu Thr Ala Ala
                            645                 650                 655

Ser Gly Ile Asp Ala Leu Thr His Ala Leu Glu Ala Tyr Val Ser Met
                        660                 665                 670

Leu Ala Thr Asp Tyr Thr Asp Ser Leu Ala Leu Arg Ala Ile Lys Met
                    675                 680                 685

Ile Phe Glu Tyr Leu Pro Arg Ala Tyr Glu Asn Gly Ala Ser Asp Leu
                690                 695                 700

Val Ala Arg Glu Lys Met Ala Asn Ala Ala Thr Ile Ala Gly Met Ala
        705                 710                 715                 720

Phe Ala Asn Ala Phe Leu Gly Val Cys His Ser Met Ala Arg Lys Leu
                            725                 730                 735

Gly Ala Phe Tyr His Leu Pro His Gly Val Ala Asn Ala Leu Met Ile
                        740                 745                 750

Asn Glu Val Ile Arg Phe Asn Ser Ser Glu Ala Pro Thr Lys Met Gly
                    755                 760                 765

Thr Phe Pro Gln Tyr Asp His Pro Arg Thr Leu Glu Arg Tyr Ala Glu
                770                 775                 780

Ile Ala Asp Tyr Ile Gly Leu Lys Gly Lys Asn Asn Glu Glu Lys Val
        785                 790                 795                 800

Glu Asn Leu Ile Lys Ala Ile Asp Glu Leu Lys Glu Lys Val Gly Ile
                            805                 810                 815
```

```
Arg Lys Thr Ile Lys Asp Tyr Asp Ile Asp Glu Lys Glu Phe Leu Asp
            820                 825                 830

Arg Leu Asp Glu Met Val Glu Gln Ala Phe Asp Asp Gln Cys Thr Gly
        835                 840                 845

Thr Asn Pro Arg Tyr Pro Leu Met Asn Glu Ile Arg Gln Met Tyr Leu
850                 855                 860

Asn Ala Tyr Tyr Gly Gly Ala Lys Lys
865                 870

<210> SEQ ID NO 3
<211> LENGTH: 2622
<212> TYPE: DNA
<213> ORGANISM: Clostridium thermocellum

<400> SEQUENCE: 3
atgacgaaaa tagcgaataa atacgaagtt attgataatg ttgaaaagct tgaaaaggct      60
ttgaaacgtt taagagaagc tcaaagtgtt tatgcaacct atacacagga gcaggttgac    120
aaaattttct ttgaggcggc aatggcggcc aataaaatga aattcctct tgccaaaatg      180 gctgtggagg aaacaggcat gggagtggtt gaagacaagg ttatcaaaaa ccactatgct    240
tctgagtata tctataatgc gtacaaaaac actaaaacct gcggtgttat tgaagaggac    300
cctgctttcg gtattaaaaa aatagcgaga cctttgggg ttattgcggc ggttataccct    360 actacgaatc cgacatcgac agcaatcttt aagactctta ttgcattaaa gacgagaaat    420
gcaattatta taagcccaca ccccaggca aaaaactcaa cgatagaagc ggcgaaaatt      480
gttttggagg cggccgttaa agccggtgct ccggaaggca tcattggctg gattgatgtg    540
ccgagccttg aacttaccaa cctggtaatg agagaagcag atgtgattct cgcaacaggc    600
ggtcccggac tggttaaagc agcttactct tcgggcaaac cggctattgg tgtcggagcg    660
ggcaatactc ctgcaattat tgatgattcg gccgacattg tcttggcagt gaactcaata    720
atacattcaa aaactttcga caacggtatg atttgtgctt cagagcaatc ggtcattgtt    780
ctggacgggg tatataaaga ggtaaaaaaa gaatttgaaa aagaggatg ctatttctta    840 aatgaagatg aaactgaaaa ggtaagaaaa acaattataa taaacggtgc gttaaatgcc    900
aagatagtag gtcagaaagc tcacacaatt gcaaaccttg caggtttga ggtacccgag    960 actacaaaaa ttctgatagg cgaagttacc agcgtggata tttccgaaga atttgcccac  1020
gaaaagttgt gcccggtact ggcaatgtac agggcaaagg attttgacga tgcccttgat  1080
aaagcagaaa ggttggtagc tgacggtgga tttggcccata cttcgtcact ttatatagat  1140
acggtaacac agaaagagaa acttcagaaa ttctctgaaa ggatgaaaac ctgccgtata  1200
ttggttaata cgccgtcatc ccagggaggt atcggtgacc tttacaactt caagcttgct  1260
ccgtctctca ccctcggctg cggttcctgg ggaggaaatt cagtttccga caatgtggga  1320
gtcaagcatt tgttaaacat taaaacagtt gccgagagga gagagaacat gctctggttc  1380
agaacacctg aaaagattta tataaaaaga ggttgtctgc ctgttgcatt ggatgagctt  1440
aaaaatgtaa tgggtaaaaa gaaagcattt attgtaacgg ataacttcct gtacaataac  1500
ggctacacca agccgattac ggataagctg gatgaaatgg gaattgtgca aagaccttc   1560 tttgatgtgt ctccagaccc atcccttgca tctgccaaag ccggtgcggc agaaatgctg  1620
gctttccagc ctgacaccat aattgcggtc ggcggcggat ctgccatgga cgcggccaaa  1680
atcatgtggg tgatgtatga acatccggaa gttgacttta tggacatggc aatgagattt  1740
atggatataa gaaagagagt ttacaccttc ccgaagatgg gacagaaggc atactttatc  1800
```

```
gcaattccga cttccgcggg tacaggttca gaagtgacac cttttgcggt tattactgat    1860
gaaaaaacag gaattaaata ccctctggcc gactatgaat tgttgccgga catggctatt    1920
gtagatgccg atatgatgat gaatgctcca aagggactta ccgcagcttc cggtatagac    1980
gcattgaccc acgctctgga agccatgtt tcaatgcttg cgaccgacta tacggatagc    2040
cttgcccttc gtgcaataaa gatgatattt gaatatctcc cgagagccta tgaaaacggt    2100
gcaagtgacc cggttgcaag agagaaaatg gccaatgccg caacaatagc cggaatggct    2160
tttgccaatg cctttttggg tgtatgccat tcaatggcgc acaaactggg tgcttttat    2220 cacctgcccc acggtgttgc caatgcactt atgataaacg aagtaatcag attcaactca    2280
tccgaggctc cgaccaagat gggtactttc ccgcagtatg accatccgcg cacgctggaa    2340
aggtatgcag aaattgccga ttatatcgga cttaagggca agaataacga agaaaaagtt    2400
gaaaacttga ttaaagctat tgatgagctt aaagaaaagg tgggcatcag gaagaccatc    2460
aaagattatg acatagatga aaaggaattt tggacagac tggacgaaat ggtggaacag    2520
gcttttgacg accagtgcac aggtacaaat ccaagatacc cgcttatgaa tgaaatcagg    2580
caaatgtatc tgaacgctta ttacggaggt gcgaagaaat ga                      2622

<210> SEQ ID NO 4
<211> LENGTH: 2622
<212> TYPE: DNA
<213> ORGANISM: Clostridium thermocellum

<400> SEQUENCE: 4
atgacgaaaa tagcgaataa atacgaagtt attgataatg ttgaaaagct tgaaaaggct      60
ttgaaacgtt taagagaagc tcaaagtgtt tatgcaaccct atacacagga gcaggttgac    120 aaaatttct ttgaggcggc aatggcggcc aataaaatga gaattcctct tgccaaaatg     180
gctgtggagg aaacaggcat gggagtggtt gaagacaagg ttatcaaaaa ccactatgct    240
tctgagtata tctataatgc gtacaaaaac actaaaacct gcggtgttat tgaagaggac    300
cctgctttcg gtattaaaaa aatagcagag ccttttgggg ttattgcggc ggttatacct    360
actacgaatc cgacatcgac agcaatcttt aagactctta ttgcattaaa gacgagaaat    420
gcaattatta taagcccaca ccccagggca aaaaactcaa cgatagaagc ggcgaaaatt    480
gttttggagg cggccgttaa agccggtgct ccggaaggca tcattggctg gattgatgtg    540
ccgagccttg aacttaccaa cctggtaatg agagaagcag atgtgattct cgcaacaggc    600
ggtcccggac tggttaaagc agcttactct tcgggcaaac cggctattgg tgtcggagcg    660
ggcaatactc ctgcaattat tgatgattcg gccgacattg tcttggcagt gaactcaata    720
atacattcaa aactttcga caacggtatg atttgtgctt cagagcaatc ggtcattgtt    780
ctggacgggg tatataaaga ggtaaaaaaa gaatttgaaa aagaggatg ctatttctta    840 aatgaagatg aaactgaaaa ggtaagaaaa acaattataa taaacggtgc gttaaatgcc    900
aagatagtag gtcagaaagc tcacacaatt gcaaaccttg caggttttga ggtacccgag    960
actacaaaaa ttctgatagg cgaagttacc agcgtggata tttccgaaga atttgcccac   1020
gaaaagttgt gcccggtact ggcaatgtac agggcaaagg atttgacga tgcccttgat   1080 aaagcagaaa ggttggtagc tgacggtgga tttggccata cttcgtcact ttatatagat   1140
acggtaacac agaaagagaa acttcagaaa ttctctgaaa ggatgaaaac ctgccgtata   1200
ttggttaata cgccgtcatc ccagggaggt atcggtgacc tttacaactt caagcttgct   1260
ccgtctctca ccctcggctg cggttcctgg ggaggaaatt cagtttccga caatgtggga   1320
```

```
gtcaagcatt tgttaaacat taaaacagtt gccgagagga gagagaacat gctctggttc    1380
agaacacctg aaaagattta tataaaaaga ggttgtctgc ctgttgcatt ggatgagctt    1440
aaaaatgtaa tgggtaaaaa gaaagcattt attgtaacgg ataacttcct gtacaataac    1500
ggctacacca agccgattac ggataagctg gatgaaatgg gaattgtgca caagaccttc    1560
tttgatgtgt ctccagaccc atcccttgca tctgccaaag ccggtgcggc agaaatgctg    1620
gctttccagc ctgacaccat aattgcggtc ggcggcggat ctgccatgga cgcggccaaa    1680
atcatgtggg tgatgtatga acatccggaa gttgacttta tggacatggc aatgagattt    1740
atggatataa gaaagagagt ttacacccttc ccgaagatgg gacagaaggc atactttatc    1800
gcaattccga cttccgcggg tacaggttca gaagtgacac cttttgcggt tattactgat    1860
gaaaaaacag gaattaaaata ccctctggcc gactatgaat tgttgccgga catggctatt    1920
gtagatgccg atatgatgat gaatgctcca aagggactta ccgcagcttc cggtatagac    1980
gcattgaccc acgctctgga agcctatgtt tcaatgcttg cgaccgacta tacggatagc    2040
cttgcccttc gtgcaataaa gatgatattt gaatatctcc cgagagccta tgaaaacggt    2100
gcaagtgacc tggttgcaag agagaaaatg gccaatgccg caacaatagc cggaatggct    2160
tttgccaatg ccttttttggg tgtatgccat tcaatggcgc gcaaactggg tgcttttttat    2220 cacctgcccc acgtgttgc caatgcactt atgataaacg aagtaatcag attcaactca    2280
tccgaggctc cgaccaagat gggtactttc ccgcagtatg accatccgcg cacgctggaa    2340
aggtatgcag aaattgccga ttatatcgga cttaagggca agaataacga agaaaaagtt    2400
gaaaacttga ttaaagctat tgatgagctt aaagaaaagg tgggcatcag gaagaccatc    2460
aaagattatg acatagatga aaaggaattt ttggacagac tggacgaaat ggtgaacag    2520 gcttttgacg accagtgcac aggtacaaat ccaagatacc cgcttatgaa tgaaatcagg    2580
caaatgtatc tgaacgctta ttacggaggt gcgaagaaat ga                      2622
```

<210> SEQ ID NO 5
<211> LENGTH: 7854
<212> TYPE: DNA
<213> ORGANISM: Artificial Sequence
<220> FEATURE:
<223> OTHER INFORMATION: Plasmid pAMG205

<400> SEQUENCE: 5

```
aaacccgctg atcctagagg gccgcatcat gtaattagtt atgtcacgct tacattcacg     60 ccctccccccc acatccgctc taaccgaaaa ggaaggagtt agacaacctg aagtctaggt    120
ccctatttat ttttttatag ttatgttagt attaagaacg ttatttatat ttcaaatttt    180 tcttttttttt ctgtacagac gcgtgtacgc atgtaacatt atactgaaaa ccttgcttga    240
gaaggttttg ggacgctcga aggctttaat ttgcaagctg cggccctgca ttaatgaatc    300
ggccaacgcg cggggagagg cggtttgcgt attgggcgct cttccgcttc ctcgctcact    360
gactcgctgc gctcggtcgt tcggctgcgg cgagcggtat cagctcactc aaaggcggta    420
atacggttat ccacagaatc aggggataac gcaggaaaga acatgtgagc aaaaggccag    480
caaaagccca ggaaccgtaa aaaggccgcg ttgctggcgt ttttccatag gctccgcccc    540
cctgacgagc atcacaaaaa tcgacgctca agtcagaggt ggcgaaaccc gacaggacta    600
taaagatacc aggcgtttcc ccctggaagc tccctcgtgc gctctcctgt tccgaccctg    660
ccgcttaccg gatacctgtc cgcctttctc ccttcgggaa gcgtggcgct ttctcatagc    720
tcacgctgta ggtatctcag ttcggtgtag gtcgttcgct ccaagctggg ctgtgtgcac    780
```

```
gaaccccccg ttcagcccga ccgctgcgcc ttatccggta actatcgtct tgagtccaac    840
ccggtaagac acgacttatc gccactggca gcagccactg gtaacaggat tagcagagcg    900
aggtatgtag gcggtgctac agagttcttg aagtggtggc ctaactacgg ctacactaga    960
aggacagtat ttggtatctg cgctctgctg aagccagtta ccttcggaaa aagagttggt   1020
agctcttgat ccggcaaaca accaccgct ggtagcggtg ttttttttgt ttgcaagcag   1080
cagattacgc gcagaaaaaa aggatctcaa gaagatcctt tgatcttttc tacggggtct   1140
gacgctcagt ggaacgaaaa ctcacgttaa gggattttgg tcatgagatt atcaaaaagg   1200
atcttcacct agatcctttt aaattaaaaa tgaagtttta aatcaatcta agtatatat    1260 gagtaaactt ggtctgacag ttaccaatgc ttaatcagtg aggcacctat ctcagcgatc   1320
tgtctatttc gttcatccat agttgcctga ctccccgtcg tgtagataac tacgatacgg   1380
gagcgcttac catctggccc cagtgctgca atgataccgc gagacccacg ctcaccggct   1440
ccagatttat cagcaataaa ccagccagcc ggaagggccg agcgcagaag tggtcctgca   1500
actttatccg cctccatcca gtctattaat tgttgccggg aagctagagt aagtagttcg   1560
ccagttaata gtttgcgcaa cgttgttggc attgctacag gcatcgtggt gtcactctcg   1620
tcgtttggta tggcttcatt cagctccggt tcccaacgat caaggcgagt tacatgatcc   1680
cccatgttgt gcaaaaaagc ggttagctcc ttcggtcctc cgatcgttgt cagaagtaag   1740
ttggccgcag tgttatcact catggttatg gcagcactgc ataattctct tactgtcatg   1800
ccatccgtaa gatgcttttc tgtgactggt gagtactcaa ccaagtcatt ctgagaatag   1860
tgtatgcggc gaccgagttg ctcttgcccg gcgtcaatac gggataatag tgtatcacat   1920
agcagaactt taaaagtgct catcattgga aaacgttctt cggggcgaaa actctcaagg   1980
atcttaccgc tgttgagatc cagttcgatg taacccactc gtgcacccaa ctgatcttca   2040
gcatctttta cttcaccag cgtttctggg tgagcaaaaa caggaaggca aaatgccgca   2100
aaaaagggaa taagggcgac acggaaatgt tgaatactca tactcttcct ttttcaatgg   2160
gtaataactg atataattaa attgaagctc taatttgtga gtttagtata catgcattta   2220
cttataatac agttttttag ttttgctggc cgcatcttct caaatatgct tcccagcctg   2280
cttttctgta acgttcaccc tctaccttag catcccttcc ctttgcaaat agtcctcttc   2340
caacaataat aatgtcagat cctgtagaga ccacatcatc cacggttcta tactgttgac   2400
ccaatgcgtc tcccttgtca tctaaaccca caccgggtgt cataatcaac caatcgtaac   2460
cttcatctct tccacccatg tctctttgag caataaagcc gataacaaaa tctttgtcgc   2520
tcttcgcaat gtcaacagta cccttagtat attctccagt agatagggag cccttgcatg   2580
acaattctgc taacatcaaa aggcctctag gttcctttgt tacttcttct gccgcctgct   2640
tcaaaccgct aacaatacct gggcccacca caccgtgtgc attcgtaatg tctgcccatt   2700
ctgctattct gtatacaccc gcagagtact gcaatttgac tgtattacca atgtcagcaa   2760
attttctgtc ttcgaagagt aaaaaattgt acttggcgga taatgccttt agcggcttaa   2820
ctgtgccctc catggaaaaa tcagtcaaga tatccacatg tgttttttagt aaacaaattt   2880 tgggacctaa tgcttcaact aactccagta attccttggt ggtacgaaca tccaatgaag   2940
cacacaagtt tgtttgcttt tcgtgcatga tattaaatag cttggcagca acaggactag   3000
gatgagtagc agcacgttcc ttatatgtag cttttcgaca tgatttatctt cgtttcctgc   3060 aggtttttgt tctgtgcagt tgggttaaga atactgggca atttcatgtt tcttcaacac   3120
tacatatgcg tatatatacc aatctaagtc tgtgctcctt ccttcgttct tccttctgtt   3180
```

```
cggagattac cgaatcaaaa aaatttcaaa gaaaccgaaa tcaaaaaaaa gaataaaaaa      3240
aaaatgatga attgaattga aaagctagct tatcgatggg tccttttcat cacgtgctat      3300
aaaaataatt ataatttaaa ttttttaata taaatatata aattaaaaat agaaagtaaa      3360
aaaagaaatt aaagaaaaaa tagttttttgt tttccgaaga tgtaaaagac tctagggga      3420
tcgccaacaa atactacctt ttatcttgct cttcctgctc tcaggtatta atgccgaatt      3480
gtttcatctt gtctgtgtag aagaccacac acgaaaatcc tgtgatttta cattttactt      3540
atcgttaatc gaatgtatat ctatttaatc tgcttttctt gtctaataaa tatatatgta      3600
aagtacgctt tttgttgaaa ttttttaaac ctttgtttat ttttttttct tcattccgta      3660
actcttctac cttctttatt tactttctaa aatccaaata caaaacataa aaataaataa      3720
acacagagta aattcccaaa ttattccatc attaaaagat acgaggcgcg tgtaagttac      3780
aggcaagcga tccgtccgcc ggcgaacgtg gcgagaaagg aagggaagaa agcgaaagga      3840
gcggggcta gggcggtggg aagtgtaggg gtcacgctgg gcgtaaccac cacacccgcc      3900
gcgcttaatg gggcgctaca gggcgcgtgg ggatgatcca ctagtgaatt taggaggctt      3960
acttgtctgc tttcttcatt agaatcaatc cttttttaaa agtcaatccc gtttgttgaa      4020
ctactcttta ataaaataat ttttccgttc ccaattccac attgcaataa tagaaaatcc      4080
atcttcatcg gcttttttcgt catcatctgt atgaatcaaa tcgccttctt ctgtgtcatc      4140
aaggtttaat ttttttatgta tttcttttaa caaaccacca taggagatta accttttacg      4200
gtgtaaacct tcctccaaat cagacaaacg tttcaaattc ttttcttcat catcggtcat      4260
aaaatccgta tccttacag gatattttgc agtttcgtca attgccgatt gtatatccga      4320
tttatattta ttttttcggtc gaatcatttg aacttttaca tttggatcat agtctaattt      4380
cattgccttt ttccaaaatt gaatccattg ttttttgattc acgtagtttt ctgtattctt      4440
aaaataagtt ggttccacac ataccaatac atgcatgtgc tgattataag aattatcttt      4500
attatttatt gtcacttccg ttgcacgcat aaaaccaaca agatttttat taattttttt      4560
atattgcatc attcggcgaa atccttgagc catatctgac aaaactcttat ttaattcttc      4620
gccatcataa acattttttaa ctgttaatgt gagaaacaac caacgaactg ttggcttttg      4680
tttaataact tcagcaacaa cctttttgtga ctgaatgcca tgtttcattg ctctcctcca      4740
gttgcacatt ggacaaagcc tggatttaca aaaccacact cgatacaact ttctttcgcc      4800
tgtttcacga ttttgtttat actctaatat ttcagcacaa tcttttactc tttcagcctt      4860
tttaaattca agaatatgca gaagttcaaa gtaatcaaca ttagcgattt tcttttctct      4920
ccatggtctc acttttccac tttttgtctt gtccactaaa acccttgatt tttcatctga      4980
ataaatgcta ctattaggac acataatatt aaaagaaacc cccatctatt tagttatttg      5040
tttggtcact tataactttta acagatgggg ttttttctgtg caaccaattt taagggtttt      5100
caatacttta aaacacatac ataccaacac ttcaacgcac ctttcagcaa ctaaaataaa      5160
aatgacgtta tttctatatg tatcaagaat agaaagaact cgttttttcgc tacgctcaaa      5220
acgcaaaaaa agcactcatt cgagtgcttt ttccttatcgc tccaaatcat gcgattttt       5280
cctctttgct tttctttgct cacgaagttc tcgatcacgc tgcaaaacat cttgaagcga      5340
aaagtattc ttctttttctt ccgatcgctc atgctgacgc acgaaaagcc tctaggcgc       5400
ataggaacaa ctcctaaatg catgtgaggg gttttctcgt ccatgtgaac agtcgcatac      5460
gcaatatttt gtttcccata gctagtaagc ttggatcctc gcgaggccgg ccagtattct      5520
gacatgggtg tatcaataac ccatgcgttt ccgtattgta tcggaatggt ttcggacagg      5580
```

-continued

```
gcggtgggaa tagacatgga aaagattttt ttgcccgagg atgcattgat aaagtatttc   5640
ttttccgaaa gagaggaaaa gattctaaag agttttggaa atactgatga atattgtgtg   5700
cagagtacaa ttctatggac aagaaaagag gctttgtcaa aacttttcg tctgggaatg    5760 aggatggatt ttaaaaagct ggatactttg gaggacgagg tggttttca ggaaacaaac    5820 agggcgcgtc tgttttcttt tatatgcaat aattactgta tctctctggc attgccaggt   5880
tttaataaag attaaaatta ttgactagaa ataaaaaat tgtccataat attaatggac     5940
aaaaaaacaa agaattacat caaaggaaga taaaaatact ttgttaaaaa attaattatt   6000
ttttatctaa actattgaaa atgaaaataa aataatataa aatgaatcat agtgcaagag   6060
atacttgcca gaggatgaat attttactgc attcatgctt tatggcagct aatagaggca   6120
ttaaattaaa ttttaattta caataggagg cgatattaat gaactttaat aaaattgatt   6180
tagacaattg gaagagaaaa gagatattta atcattattt gaaccaacaa acgactttta   6240
gtataaccac agaaattgat attagtgttt tataccgaaa cataaaacaa gaaggatata   6300
aattttaccc tgcatttatt ttcttagtga caagggtgat aaactcaaat acagctttta   6360
gaactggtta caatagcgac ggagagttag gttattggga taagtagag ccactttata    6420 caatttttga tggtgtatct aaaacattct ctggtatttg gactcctgta aagaatgact   6480
tcaaagagtt ttatgattta tacctttctg atgtagagaa atataatggt tcggggaaat   6540
tgtttcccaa aacacctata cctgaaaatg cttttctct ttctattatt ccatggactt     6600
catttactgg gttaaactta aatatcaata ataaagtaa ttaccttcta cccattatta    6660
cagcaggaaa attcattaat aaaggtaatt caatatattt accgctatct ttacaggtac   6720
atcattctgt ttgtgatggt tatcatgcag gattgtttat gaactctatt caggaattgt   6780
cagataggcc taatgactgg cttttataat aaaggaggtc gacgtcatgt ttattgatac   6840
attaattgaa aagattagag aaaaggataa tccttccgtt gtaggattag accctaaaat    6900
tgaatatgtt ccgtctttta taaaggaaga catgtataaa aaatacggga aaatttaaa    6960 agctgtggca gaggcgattc tcctcttcaa taaatatatt attgatgcgg tttacgatat   7020
tgttcctgca gtaaaaccgc agcttgcata ttatgaaatg tacggccttg aaggcatgag   7080
ggtgttttat gaaacttgca aatatgcaaa ggaaaaagga ctttggtta ttgcagacgg     7140 aaaaagaaac gacataggtt ccaccgccca gtgttattct gccgcatatc ttggaaaaac   7200
ggacattgat gaaggtataa gcgaggcggt ttttgatgtg gatgccctga cagtcaaccc   7260
gtatcttggt gtggacggta ttaagccttt tatagatgac tgtgtcaagt acaacaaggg   7320
catatttgtt ctggtcaaga catcaaacaa gtcatccgga gaaattcagg acatactcac   7380
ccaggaagga agaagcattt atgagattgt tgcggagtat gttgaatcat ggggtgaaaa   7440
caaaaaagga aaatatggat acagttgtgt gggagcagtg gttggagcaa cttatcccaa   7500
tctggccaaa attttaagaa agattctgaa aaattcctat atactggttc cgggctatgg   7560
agctcaggga ggaacagcca gagatgtagc ccattgcttt aattatgacg ggctcggagc   7620
aattgtcaat gcatcaagaa gcataatgtg tgcctacaaa tctgaacaat ggaagaatgt   7680
ttacagcgaa gaaaagtttt atgaggcatc aagagccgag gcaataagaa tgagggacga   7740
tattaacagt gcgttgcgag acaggaagta agcccgggcc tcgagaaaac aaaaggctca   7800
gtcggaagac tgggcctttt gttttggtac cgaattcggc gcgcctcagc gttt          7854
```

<210> SEQ ID NO 6
<211> LENGTH: 873
<212> TYPE: PRT

<213> ORGANISM: Clostridium thermocellum

<400> SEQUENCE: 6

```
Met Thr Lys Ile Ala Asn Lys Tyr Glu Val Ile Asp Asn Val Glu Lys
1               5                   10                  15

Leu Glu Lys Ala Leu Lys Arg Leu Arg Glu Ala Gln Ser Val Tyr Ala
            20                  25                  30

Thr Tyr Thr Gln Glu Gln Val Asp Lys Ile Phe Phe Glu Ala Ala Met
        35                  40                  45

Ala Ala Asn Lys Met Arg Ile Pro Leu Ala Lys Met Ala Val Glu Glu
    50                  55                  60

Thr Gly Met Gly Val Val Glu Asp Lys Val Ile Lys Asn His Tyr Ala
65                  70                  75                  80

Ser Glu Tyr Ile Tyr Asn Ala Tyr Lys Asn Thr Lys Thr Cys Gly Val
                85                  90                  95

Ile Glu Glu Asp Pro Ala Phe Gly Ile Lys Lys Ile Ala Glu Pro Leu
            100                 105                 110

Gly Val Ile Ala Ala Val Ile Pro Thr Thr Asn Pro Thr Ser Thr Ala
        115                 120                 125

Ile Phe Lys Thr Leu Ile Ala Leu Lys Thr Arg Asn Ala Ile Ile Ile
    130                 135                 140

Ser Pro His Pro Arg Ala Lys Asn Ser Thr Ile Glu Ala Ala Lys Ile
145                 150                 155                 160

Val Leu Glu Ala Ala Val Lys Ala Gly Ala Pro Glu Gly Ile Ile Gly
                165                 170                 175

Trp Ile Asp Val Pro Ser Leu Glu Leu Thr Asn Leu Val Met Arg Glu
            180                 185                 190

Ala Asp Val Ile Leu Ala Thr Gly Gly Pro Gly Leu Val Lys Ala Ala
        195                 200                 205

Tyr Ser Ser Gly Lys Pro Ala Ile Gly Val Gly Ala Gly Asn Thr Pro
    210                 215                 220

Ala Ile Ile Asp Asp Ser Ala Asp Ile Val Leu Ala Val Asn Ser Ile
225                 230                 235                 240

Ile His Ser Lys Thr Phe Asp Asn Gly Met Ile Cys Ala Ser Glu Gln
                245                 250                 255

Ser Val Ile Val Leu Asp Gly Val Tyr Lys Glu Val Lys Lys Glu Phe
            260                 265                 270

Glu Lys Arg Gly Cys Tyr Phe Leu Asn Glu Asp Glu Thr Glu Lys Val
        275                 280                 285

Arg Lys Thr Ile Ile Asn Gly Ala Leu Asn Ala Lys Ile Val Gly
    290                 295                 300

Gln Lys Ala His Thr Ile Ala Asn Leu Ala Gly Phe Glu Val Pro Glu
305                 310                 315                 320

Thr Thr Lys Ile Leu Ile Gly Glu Val Thr Ser Val Asp Ile Ser Glu
                325                 330                 335

Glu Phe Ala His Glu Lys Leu Cys Pro Val Leu Ala Met Tyr Arg Ala
            340                 345                 350

Lys Asp Phe Asp Asp Ala Leu Asp Lys Ala Glu Arg Leu Val Ala Asp
        355                 360                 365

Gly Gly Phe Gly His Thr Ser Ser Leu Tyr Ile Asp Thr Val Thr Gln
    370                 375                 380

Lys Glu Lys Leu Gln Lys Phe Ser Glu Arg Met Lys Thr Cys Arg Ile
385                 390                 395                 400

Leu Val Asn Thr Pro Ser Ser Gln Gly Gly Ile Gly Asp Leu Tyr Asn
```

```
                405                 410                 415
Phe Lys Leu Ala Pro Ser Leu Thr Leu Gly Cys Gly Ser Trp Gly Gly
                420                 425                 430

Asn Ser Val Ser Asp Asn Val Gly Val Lys His Leu Leu Asn Ile Lys
                435                 440                 445

Thr Val Ala Glu Arg Arg Glu Asn Met Leu Trp Phe Arg Thr Pro Glu
            450                 455                 460

Lys Ile Tyr Ile Lys Arg Gly Cys Leu Pro Val Ala Leu Asp Glu Leu
465                 470                 475                 480

Lys Asn Val Met Gly Lys Lys Ala Phe Ile Val Thr Asp Asn Phe
                485                 490                 495

Leu Tyr Asn Asn Gly Tyr Thr Lys Pro Ile Thr Asp Lys Leu Asp Glu
                500                 505                 510

Met Gly Ile Val His Lys Thr Phe Phe Asp Val Ser Pro Asp Pro Ser
                515                 520                 525

Leu Ala Ser Ala Lys Ala Gly Ala Ala Glu Met Leu Ala Phe Gln Pro
                530                 535                 540

Asp Thr Ile Ile Ala Val Gly Gly Arg Ser Ala Met Asp Ala Ala Lys
545                 550                 555                 560

Ile Met Trp Val Met Tyr Glu His Pro Glu Val Asp Phe Met Asp Met
                565                 570                 575

Ala Met Arg Phe Met Asp Ile Arg Lys Arg Val Tyr Thr Phe Pro Lys
                580                 585                 590

Met Gly Gln Lys Ala Tyr Phe Ile Ala Ile Pro Thr Ser Ala Gly Thr
                595                 600                 605

Gly Ser Glu Val Thr Pro Phe Ala Val Ile Thr Asp Glu Lys Thr Gly
                610                 615                 620

Ile Lys Tyr Pro Leu Ala Asp Tyr Glu Leu Leu Pro Asp Met Ala Ile
625                 630                 635                 640

Val Asp Ala Asp Met Met Met Asn Ala Pro Lys Gly Leu Thr Ala Ala
                645                 650                 655

Ser Gly Ile Asp Ala Leu Thr His Ala Leu Glu Ala Tyr Val Ser Met
                660                 665                 670

Leu Ala Thr Asp Tyr Thr Asp Ser Leu Ala Leu Arg Ala Ile Lys Met
                675                 680                 685

Ile Phe Glu Tyr Leu Pro Arg Ala Tyr Glu Asn Gly Ala Ser Asp Pro
                690                 695                 700

Val Ala Arg Glu Lys Met Ala Asn Ala Ala Thr Ile Ala Gly Met Ala
705                 710                 715                 720

Phe Ala Asn Ala Phe Leu Gly Val Cys His Ser Met Ala His Lys Leu
                725                 730                 735

Gly Ala Phe Tyr His Leu Pro His Gly Val Ala Asn Ala Leu Met Ile
                740                 745                 750

Asn Glu Val Ile Arg Phe Asn Ser Ser Glu Ala Pro Thr Lys Met Gly
                755                 760                 765

Thr Phe Pro Gln Tyr Asp His Pro Arg Thr Leu Glu Arg Tyr Ala Glu
                770                 775                 780

Ile Ala Asp Tyr Ile Gly Leu Lys Gly Lys Asn Asn Glu Glu Lys Val
785                 790                 795                 800

Glu Asn Leu Ile Lys Ala Ile Asp Glu Leu Lys Glu Lys Val Gly Ile
                805                 810                 815

Arg Lys Thr Ile Lys Asp Tyr Asp Ile Asp Lys Glu Lys Phe Leu Asp
                820                 825                 830
```

```
Arg Leu Asp Glu Met Val Glu Gln Ala Phe Asp Asp Gln Cys Thr Gly
        835                 840                 845
Thr Asn Pro Arg Tyr Pro Leu Met Asn Glu Ile Arg Gln Met Tyr Leu
    850                 855                 860
Asn Ala Tyr Tyr Gly Gly Ala Lys Lys
865                 870

<210> SEQ ID NO 7
<211> LENGTH: 873
<212> TYPE: PRT
<213> ORGANISM: Clostridium thermocellum

<400> SEQUENCE: 7

Met Thr Lys Ile Ala Asn Lys Tyr Glu Val Ile Asp Asn Val Glu Lys
1               5                   10                  15
Leu Glu Lys Ala Leu Lys Arg Leu Arg Glu Ala Gln Ser Val Tyr Ala
                20                  25                  30
Thr Tyr Thr Gln Glu Gln Val Asp Lys Ile Phe Phe Glu Ala Ala Met
            35                  40                  45
Ala Ala Asn Lys Met Arg Ile Pro Leu Ala Lys Met Ala Val Glu Glu
        50                  55                  60
Thr Gly Met Gly Val Val Glu Asp Lys Val Ile Lys Asn His Tyr Ala
65                  70                  75                  80
Ser Glu Tyr Ile Tyr Asn Ala Tyr Lys Asn Thr Lys Thr Cys Gly Val
                85                  90                  95
Ile Glu Glu Asp Pro Ala Phe Gly Ile Lys Lys Ile Ala Glu Pro Leu
            100                 105                 110
Gly Val Ile Ala Ala Val Ile Pro Thr Thr Asn Pro Thr Ser Thr Ala
        115                 120                 125
Ile Phe Lys Thr Leu Ile Ala Leu Lys Thr Arg Asn Ala Ile Ile Ile
    130                 135                 140
Ser Pro His Pro Arg Ala Lys Asn Ser Thr Ile Glu Ala Ala Lys Ile
145                 150                 155                 160
Val Leu Glu Ala Ala Val Lys Ala Gly Ala Pro Glu Gly Ile Ile Gly
                165                 170                 175
Trp Ile Asp Val Pro Ser Leu Glu Leu Thr Asn Leu Val Met Arg Glu
            180                 185                 190
Ala Asp Val Ile Leu Ala Thr Gly Gly Pro Gly Leu Val Lys Ala Ala
        195                 200                 205
Tyr Ser Ser Gly Lys Pro Ala Ile Gly Val Gly Ala Gly Asn Thr Pro
    210                 215                 220
Ala Ile Ile Asp Asp Ser Ala Asp Ile Val Leu Ala Val Asn Ser Ile
225                 230                 235                 240
Ile His Ser Lys Thr Phe Asp Asn Gly Met Ile Cys Ala Ser Glu Gln
                245                 250                 255
Ser Val Ile Val Leu Asp Gly Val Tyr Lys Glu Val Lys Lys Glu Phe
            260                 265                 270
Glu Lys Arg Gly Cys Tyr Phe Leu Asn Glu Asp Glu Thr Glu Lys Val
        275                 280                 285
Arg Lys Thr Ile Ile Ile Asn Gly Ala Leu Asn Ala Lys Ile Val Gly
    290                 295                 300
Gln Lys Ala His Thr Ile Ala Asn Leu Ala Gly Phe Glu Val Pro Glu
305                 310                 315                 320
Thr Thr Lys Ile Leu Ile Gly Glu Val Thr Ser Val Asp Ile Ser Glu
                325                 330                 335
```

-continued

```
Glu Phe Ala His Glu Lys Leu Cys Pro Val Leu Ala Met Tyr Arg Ala
            340                 345                 350
Lys Asp Phe Asp Asp Ala Leu Asp Lys Ala Glu Arg Leu Val Ala Asp
            355                 360                 365
Gly Gly Phe Gly His Thr Ser Ser Leu Tyr Ile Asp Thr Val Thr Gln
            370                 375                 380
Lys Glu Lys Leu Gln Lys Phe Ser Glu Arg Met Lys Thr Cys Arg Ile
385                 390                 395                 400
Leu Val Asn Thr Pro Ser Ser Gln Gly Gly Ile Gly Asp Leu Tyr Asn
                405                 410                 415
Phe Lys Leu Ala Pro Ser Leu Thr Leu Gly Cys Gly Ser Trp Gly Gly
            420                 425                 430
Asn Ser Val Ser Asp Asn Val Gly Val Lys His Leu Leu Asn Ile Lys
            435                 440                 445
Thr Val Ala Glu Arg Arg Glu Asn Met Leu Trp Phe Arg Thr Pro Glu
            450                 455                 460
Lys Ile Tyr Ile Lys Arg Gly Cys Leu Pro Val Ala Leu Asp Glu Leu
465                 470                 475                 480
Lys Asn Val Met Gly Lys Lys Ala Phe Ile Val Thr Gly Asn Phe
                485                 490                 495
Leu Tyr Asn Asn Gly Tyr Thr Lys Pro Ile Thr Asp Lys Leu Asp Glu
                500                 505                 510
Met Gly Ile Val His Lys Thr Phe Phe Asp Val Ser Pro Asp Pro Ser
            515                 520                 525
Leu Ala Ser Ala Lys Ala Gly Ala Ala Glu Met Leu Ala Phe Gln Pro
            530                 535                 540
Asp Thr Ile Ile Ala Val Gly Gly Gly Ser Ala Met Asp Ala Ala Lys
545                 550                 555                 560
Ile Met Trp Val Met Tyr Glu His Pro Glu Val Asp Phe Met Asp Met
                565                 570                 575
Ala Met Arg Phe Met Asp Ile Arg Lys Arg Val Tyr Thr Phe Pro Lys
            580                 585                 590
Met Gly Gln Lys Ala Tyr Phe Ile Ala Ile Pro Thr Ser Ala Gly Thr
            595                 600                 605
Gly Ser Glu Val Thr Pro Phe Ala Val Ile Thr Asp Glu Lys Thr Gly
            610                 615                 620
Ile Lys Tyr Pro Leu Ala Asp Tyr Glu Leu Leu Pro Asp Met Ala Ile
625                 630                 635                 640
Val Asp Ala Asp Met Met Met Asn Ala Pro Lys Gly Leu Thr Ala Ala
                645                 650                 655
Ser Gly Ile Asp Ala Leu Thr His Ala Leu Glu Ala Tyr Val Ser Met
            660                 665                 670
Leu Ala Thr Asp Tyr Thr Asp Ser Leu Ala Leu Arg Ala Ile Lys Met
            675                 680                 685
Ile Phe Glu Tyr Leu Pro Arg Ala Tyr Glu Asn Gly Ala Ser Asp Pro
            690                 695                 700
Val Ala Arg Glu Lys Met Ala Asn Ala Ala Thr Ile Ala Gly Met Ala
705                 710                 715                 720
Phe Ala Asn Ala Phe Leu Gly Val Cys His Ser Met Ala His Lys Leu
                725                 730                 735
Gly Ala Phe Tyr His Leu Pro His Gly Val Ala Asn Ala Leu Met Ile
            740                 745                 750
Asn Glu Val Ile Arg Phe Asn Ser Ser Glu Ala Pro Thr Lys Met Gly
            755                 760                 765
```

```
Thr Phe Pro Gln Tyr Asp His Pro Arg Thr Leu Glu Arg Tyr Ala Glu
        770                 775                 780
Ile Ala Asp Tyr Ile Gly Leu Lys Gly Lys Asn Asn Glu Glu Lys Val
785                 790                 795                 800
Glu Asn Leu Ile Lys Ala Ile Asp Glu Leu Lys Glu Lys Val Gly Ile
                805                 810                 815
Arg Lys Thr Ile Lys Asp Tyr Asp Ile Asp Glu Lys Glu Phe Leu Asp
            820                 825                 830
Arg Leu Asp Glu Met Val Glu Gln Ala Phe Asp Asp Gln Cys Thr Gly
        835                 840                 845
Thr Asn Pro Arg Tyr Pro Leu Met Asn Glu Ile Arg Gln Met Tyr Leu
    850                 855                 860
Asn Ala Tyr Tyr Gly Gly Ala Lys Lys
865                 870

<210> SEQ ID NO 8
<211> LENGTH: 2622
<212> TYPE: DNA
<213> ORGANISM: Clostridium thermocellum

<400> SEQUENCE: 8
```

| | | | | | |
|---|---|---|---|---|---|
| atgacgaaaa | tagcgaataa | atacgaagtt | attgataatg | ttgaaaagct | tgaaaaggct | 60 |
| ttgaaacgtt | taagagaagc | tcaaagtgtt | tatgcaacct | atacacagga | gcaggttgac | 120 |
| aaaattttct | tgaggcggc | aatggcggcc | aataaaatga | aattcctct | tgccaaaatg | 180 |
| gctgtggagg | aaacaggcat | gggagtggtt | gaagacaagg | ttatcaaaaa | ccactatgct | 240 |
| tctgagtata | tctataatgc | gtacaaaaac | actaaaaccct | gcggtgttat | tgaagaggac | 300 |
| cctgctttcg | gtattaaaaa | aatagcagag | cctttggggg | ttattgcggc | ggttatacct | 360 |
| actacgaatc | cgacatcgac | agcaatcttt | aagactctta | ttgcattaaa | gacgagaaat | 420 |
| gcaattatta | taagcccaca | ccccagggca | aaaaactcaa | cgatagaagc | ggcgaaaatt | 480 |
| gttttggagg | cggccgttaa | agccggtgct | ccggaaggca | tcattggctg | gattgatgtg | 540 |
| ccgagccttg | aacttaccaa | cctggtaatg | agagaagcag | atgtgattct | cgcaacaggc | 600 |
| ggtcccggac | tggttaaagc | agcttactct | tcgggcaaac | cggctattgg | tgtcggagcg | 660 |
| ggcaatactc | ctgcaattat | tgatgattcg | gccgacattg | tcttggcagt | gaactcaata | 720 |
| atacattcaa | aaactttcga | caacggtatg | atttgtgctt | cagagcaatc | ggtcattgtt | 780 |
| ctggacgggg | tatataaaga | ggtaaaaaaa | gaatttgaaa | aaagaggatg | ctatttctta | 840 |
| aatgaagatg | aaactgaaaa | ggtaagaaaa | acaattataa | taaacggtgc | gttaaatgcc | 900 |
| aagatagtag | tcagaaagc | tcacacaatt | gcaaaccttg | caggttttga | ggtacccgag | 960 |
| actacaaaaa | ttctgatagg | cgaagttacc | agcgtggata | tttccgaaga | atttgcccac | 1020 |
| gaaaagttgt | gcccggtact | ggcaatgtac | agggcaaagg | attttgacga | tgcccttgat | 1080 |
| aaagcagaaa | ggttggtagc | tgacggtgga | tttggccata | cttcgtcact | ttatatagat | 1140 |
| acggtaacac | agaaagagaa | acttcagaaa | ttctctgaaa | ggatgaaaac | ctgccgtata | 1200 |
| ttggttaata | cgccgtcatc | ccagggaggt | atcggtgacc | tttacaactt | caagcttgct | 1260 |
| ccgtctctca | ccctcggctg | cggttcctgg | ggaggaaatt | cagtttccga | caatgtggga | 1320 |
| gtcaagcatt | tgttaaacat | taaaacagtt | gccgagagga | gagagaacat | gctctggttc | 1380 |
| agaacacctg | aaaagattta | tataaaaaga | ggttgtctgc | ctgttgcatt | ggatgagctt | 1440 |
| aaaaatgtaa | tgggtaaaaa | gaaagcattt | attgtaacgg | ataacttcct | gtacaataac | 1500 |

```
ggctacacca agccgattac ggataagctg gatgaaatgg gaattgtgca caagaccttc   1560
tttgatgtgt ctccagaccc atcccttgca tctgccaaag ccggtgcggc agaaatgctg   1620
gctttccagc ctgacaccat aattgcggtc ggcggcagat ctgccatgga cgcggccaaa   1680
atcatgtggg tgatgtatga acatccggaa gttgacttta tggacatggc aatgagattt   1740
atggatataa gaagagagt ttacaccttc ccgaagatgg gacagaaggc atactttatc   1800
gcaattccga cttccgcggg tacaggttca gaagtgacac ttttgcggt tattactgat   1860 gaaaaaacag gaattaaata ccctctggcc gactatgaat tgttgccgga catggctatt   1920
gtagatgccg atatgatgat gaatgctcca aagggactta ccgcagcttc cggtatagac   1980
gcattgaccc acgctctgga agcctatgtt tcaatgcttg cgaccgacta tacggatagc   2040
cttgcccttc gtgcaataaa gatgatattt gaatatctcc cgagagccta tgaaaacggt   2100
gcaagtgacc cggttgcaag agagaaaatg gccaatgccg caacaatagc cggaatggct   2160
tttgccaatg cctttttggg tgtatgccat tcaatggcgc acaaactggg tgcttttat   2220 cacctgcccc acggtgttgc caatgcactt atgataaacg aagtaatcag attcaactca   2280
tccgaggctc cgaccaagat gggtactttc ccgcagtatg accatccgcg cacgctggaa   2340
aggtatgcag aaattgccga ttatatcgga cttaagggca agaataacga agaaaaagtt   2400
gaaaacttga ttaaagctat tgatgagctt aaagaaaagg tgggcatcag gaagaccatc   2460
aaagattatg acatagatga aaaggaattt ttggacagac tggacgaaat ggtggaacag   2520
gcttttgacg accagtgcac aggtacaaat ccaagatacc cgcttatgaa tgaaatcagg   2580
caaatgtatc tgaacgctta ttacggaggt gcgaagaaat ga   2622

<210> SEQ ID NO 9
<211> LENGTH: 2622
<212> TYPE: DNA
<213> ORGANISM: Clostridium thermocellum

<400> SEQUENCE: 9
atgacgaaaa tagcgaataa atacgaagtt attgataatg ttgaaaagct tgaaaaggct     60
ttgaaacgtt taagagaagc tcaaagtgtt tatgcaacct atacacagga gcaggttgac    120
aaaattttct ttgaggcggc aatggcggcc aataaaatga gaattcctct tgccaaaatg    180
gctgtggagg aaacaggcat gggagtggtt gaagacaagg ttatcaaaaa ccactatgct    240
tctgagtata tctataatgc gtacaaaaac actaaaacct gcggtgttat tgaagaggac    300
cctgctttcg gtattaaaaa aatagcagag ccttttgggg ttattgcggc ggttataccct    360 actacgaatc cgacatcgac agcaatcttt aagactctta ttgcattaaa gacgagaaat    420
gcaattatta taagcccaca ccccagggca aaaaactcaa cgatagaagc ggcgaaaatt    480
gttttggagg cggccgttaa agccggtgct ccggaaggca tcattggctg gattgatgtg    540
ccgagccttg aacttaccaa cctggtaatg agagaagcag atgtgattct cgcaacaggc    600
ggtcccggac tggttaaagc agcttactct tcgggcaaac cggctattgg tgtcggagcg    660
ggcaatactc ctgcaattat tgatgattcg gccgacattg tcttggcagt gaactcaata    720
atacattcaa aaactttcga caacggtatg atttgtgctt cagagcaatc ggtcattgtt    780
ctggacgggt atataaaga ggtaaaaaaa gaatttgaaa aagaggatg ctatttctta    840 aatgaagatg aaactgaaaa ggtaagaaaa acaattataa taaacggtgc gttaaatgcc    900
aagatagtag gtcagaaagc tcacacaatt gcaaaccttg caggttttga ggtacccgag    960
actacaaaaa ttctgatagg cgaagttacc agcgtggata tttccgaaga atttgcccac   1020
```

```
gaaaagttgt gcccggtact ggcaatgtac agggcaaagg attttgacga tgcccttgat    1080
aaagcagaaa ggttggtagc tgacggtgga tttggccata cttcgtcact ttatatagat    1140
acggtaacac agaaagagaa acttcagaaa ttctctgaaa ggatgaaaac ctgccgtata    1200
ttggttaata cgccgtcatc ccagggaggt atcggtgacc tttacaactt caagcttgct    1260
ccgtctctca ccctcggctg cggttcctgg ggaggaaatt cagtttccga caatgtggga    1320
gtcaagcatt tgttaaacat taaaacagtt gccgagagga gagagaacat gctctggttc    1380
agaacacctg aaaagattta tataaaaaga ggttgtctgc ctgttgcatt ggatgagctt    1440
aaaaatgtaa tgggtaaaaa gaaagcattt attgtaacgg gtaacttcct gtacaataac    1500
ggctacacca agccgattac ggataagctg gatgaaatgg gaattgtgca caagaccttc    1560
tttgatgtgt ctccagaccc atcccttgca tctgccaaag ccggtgcggc agaaatgctg    1620
gctttccagc ctgacaccat aattgcggtc ggcggcggat ctgccatgga cgcggccaaa    1680
atcatgtggg tgatgtatga acatccggaa gttgacttta tggacatggc aatgagattt    1740
atggatataa gaaagagagt ttacaccttc ccgaagatgg gacagaaggc atactttatc    1800
gcaattccga cttccgcggg tacaggttca gaagtgacac cttttgcggt tattactgat    1860
gaaaaaacag gaattaaata ccctctggcc gactatgaat tgttgccgga catggctatt    1920
gtagatgccg atatgatgat gaatgctcca aagggactta ccgcagcttc cggtatagac    1980
gcattgaccc acgctctgga agcctatgtt tcaatgcttg cgaccgacta tacggatagc    2040
cttgcccttc gtgcaataaa gatgatattt gaatatctcc cgagagccta tgaaaacggt    2100
gcaagtgacc cggttgcaag agagaaaatg gccaatgccg caacaatagc cggaatggct    2160
tttgccaatg ccttttgggg tgtatgccat tcaatggcgc acaaactggg tgcttttttat   2220 cacctgcccc acggtgttgc caatgcactt atgataaacg aagtaatcag attcaactca    2280
tccgaggctc cgaccaagat gggtactttc ccgcagtatg accatccgcg cacgctggaa    2340
aggtatgcag aaattgccga ttatatcgga cttaagggca agaataacga agaaaaagtt    2400
gaaaacttga ttaaagctat tgatgagctt aaagaaaagg tgggcatcag gaagaccatc    2460
aaagattatg acatagatga aaaggaattt ttggacagac tggacgaaat ggtggaacag    2520
gcttttgacg accagtgcac aggtacaaat ccaagatacc cgcttatgaa tgaaatcagg    2580
caaatgtatc tgaacgctta ttacggaggt gcgaagaaat ga                      2622
```